US009922168B2

(12) United States Patent
Traughber et al.

(10) Patent No.: US 9,922,168 B2
(45) Date of Patent: *Mar. 20, 2018

(54) PATIENT DEVICE FOR ADVANCED PATIENT COMMUNICATION

(71) Applicant: ELOQUENCE COMMUNICATIONS, INC., Seattle, WA (US)

(72) Inventors: Bryan James Traughber, Shaker Heights, OH (US); Lance S. Patak, Seattle, WA (US)

(73) Assignee: Eloquence Communications, Inc., Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/158,031

(22) Filed: May 18, 2016

(65) Prior Publication Data

US 2016/0267752 A1    Sep. 15, 2016

Related U.S. Application Data

(60) Division of application No. 13/460,175, filed on Apr. 30, 2012, now Pat. No. 9,361,769, which is a
(Continued)

(51) Int. Cl.
*G08B 1/08* (2006.01)
*G06F 19/00* (2018.01)
(Continued)

(52) U.S. Cl.
CPC ........ *G06F 19/3406* (2013.01); *G06F 19/322* (2013.01); *G06F 19/3487* (2013.01);
(Continued)

(58) Field of Classification Search
CPC ... A61B 5/7264; A61B 5/7267; A61B 5/7282; A61B 5/741; A61B 5/742; A61B 5/743; A61B 5/7475; A61B 7/04
See application file for complete search history.

(56) References Cited

U.S. PATENT DOCUMENTS 6,057,758 A    5/2000  Dempsey et al.
6,422,875 B1   7/2002  Patak et al.
(Continued)

FOREIGN PATENT DOCUMENTS

EP    1623666 A2    2/2006
EP    2385476 A1    11/2011
(Continued)

OTHER PUBLICATIONS

Extended European Search Report, European Application No. 12275116.7, dated Jul. 30, 2013.
(Continued)

*Primary Examiner* — Joseph Feild
*Assistant Examiner* — Rufus Point
(74) *Attorney, Agent, or Firm* — Orrick, Herrington & Sutcliffe LLP

(57) ABSTRACT

A patient communication device for advanced patient communication and methods for making and using same. According to one embodiment, a patient communication device comprises a selection input mechanism for generating a message on a display, the message reflecting a patient request and an urgency level associated with the patient request. The selection input mechanism includes one or more of a button, keyboard and a touch screen. Further, the patient communication device includes a transmitter for transmitting the message to a central processing server and a status indicator on the display, the status indicator representing a transmission status associated with the message.

22 Claims, 19 Drawing Sheets

Related U.S. Application Data continuation-in-part of application No. 11/778,974, filed on Jul. 17, 2007, now Pat. No. 8,183,987.

(60) Provisional application No. 60/831,235, filed on Jul. 17, 2006, provisional application No. 61/568,073, filed on Dec. 7, 2011.

(51) Int. Cl.
| | |
|---|---|
| *G08B 5/22* | (2006.01) |
| *G08B 25/01* | (2006.01) |
| *G06Q 50/22* | (2018.01) |
| *H04M 1/725* | (2006.01) |
| *A61B 5/00* | (2006.01) |
| *G08B 21/02* | (2006.01) |
| *G08B 25/10* | (2006.01) |

(52) U.S. Cl.
CPC ............ *G06Q 50/22* (2013.01); *G08B 5/222* (2013.01); *G08B 21/0277* (2013.01); *G08B 25/016* (2013.01); *H04M 1/72527* (2013.01); *A61B 5/0002* (2013.01); *A61B 5/0022* (2013.01); *A61B 5/7282* (2013.01); *A61B 5/7475* (2013.01); *A61B 2560/045* (2013.01); *G08B 21/0211* (2013.01); *G08B 25/10* (2013.01)

(56) References Cited

U.S. PATENT DOCUMENTS

| | | | |
|---|---|---|---|
| 6,870,484 B1 | 3/2005 | Brinsfield et al. | |
| 6,958,706 B2 | 10/2005 | Chaco et al. | |
| 6,998,978 B2* | 2/2006 | Kirkeby | G06F 19/327 340/539.11 |
| 7,043,305 B2 | 5/2006 | Kenknight et al. | |
| 7,161,484 B2* | 1/2007 | Tsoukalis | A61B 5/0002 340/539.1 |
| 7,263,669 B2* | 8/2007 | Denholm | G06F 3/0219 340/286.07 |
| 7,301,451 B2* | 11/2007 | Hastings | A61B 5/411 128/903 |
| 7,307,509 B2* | 12/2007 | Chriss | G06F 19/3418 128/903 |
| 7,316,648 B2* | 1/2008 | Kelly | G06F 19/3418 128/903 |
| 7,319,386 B2* | 1/2008 | Collins, Jr. | A61B 5/1115 340/286.07 |
| 7,382,247 B2* | 6/2008 | Welch | A61B 5/0024 340/539.1 |
| 7,598,852 B2* | 10/2009 | Chriss | G06F 19/3418 128/903 |
| 8,004,398 B2* | 8/2011 | Chriss | G06F 19/3418 128/903 |
| 8,183,987 B2* | 5/2012 | Traughber | G06Q 50/22 340/286.02 |
| 8,334,777 B2 | 12/2012 | Wilson et al. | |
| 8,478,605 B2* | 7/2013 | Miller | G06Q 50/22 705/2 |
| 2002/0039408 A1* | 4/2002 | Hall | G06Q 10/10 379/90.01 |
| 2003/0062989 A1* | 4/2003 | Tsunezumi | G06Q 10/10 340/286.07 |
| 2003/0093300 A1* | 5/2003 | Denholm | G06F 3/0219 705/2 |
| 2004/0019654 A1* | 1/2004 | Powers | G06F 19/3418 709/217 |
| 2004/0172300 A1 | 9/2004 | Mihai et al. | |
| 2004/0243444 A1* | 12/2004 | Steusloff | G06F 3/002 705/2 |
| 2005/0055242 A1 | 3/2005 | Bello et al. | |
| 2005/0185799 A1 | 8/2005 | Bertram | |
| 2005/0201345 A1 | 9/2005 | Williamson | |
| 2005/0220084 A1 | 10/2005 | Parker et al. | |
| 2005/0228693 A1 | 10/2005 | Webb et al. | |
| 2005/0242928 A1 | 11/2005 | Kirkeby | |
| 2005/0277872 A1* | 12/2005 | Colby, Jr. | A61B 5/411 604/67 |
| 2006/0049936 A1* | 3/2006 | Collins, Jr. | A61B 5/1115 340/539.11 |
| 2006/0179452 A1* | 8/2006 | Amodeo | G06F 17/30011 725/25 |
| 2006/0277066 A1* | 12/2006 | Hungerford | G06F 19/322 705/2 |
| 2006/0277070 A1* | 12/2006 | Hungerford | G06F 19/322 705/3 |
| 2006/0277074 A1 | 12/2006 | Einav et al. | |
| 2006/0293571 A1 | 12/2006 | Bao et al. | |
| 2007/0038628 A1* | 2/2007 | Eckert | G06Q 10/10 |
| 2007/0094045 A1* | 4/2007 | Cobbs | G06F 19/327 705/2 |
| 2008/0018436 A1* | 1/2008 | Traughber | G06Q 50/22 340/286.07 |
| 2008/0055071 A1* | 3/2008 | Chriss | G06F 19/3418 340/539.12 |
| 2008/0059250 A1 | 3/2008 | Joao | |
| 2008/0281168 A1* | 11/2008 | Gibson | A61B 5/0205 600/301 |
| 2009/0058635 A1* | 3/2009 | LaLonde | A61N 1/37282 340/539.11 |
| 2009/0124917 A1 | 5/2009 | Hatlestad et al. | |
| 2009/0213852 A1* | 8/2009 | Krishnamurthi | H04L 51/14 370/389 |
| 2009/0248437 A1 | 10/2009 | Gucciardi et al. | |
| 2011/0022411 A1 | 1/2011 | Hjelm et al. | |
| 2011/0205062 A1 | 8/2011 | Pesot et al. | |
| 2012/0169467 A1* | 7/2012 | Condra | G06F 19/3418 340/8.1 |
| 2012/0264374 A1 | 10/2012 | Perkins et al. | |
| 2015/0178502 A1* | 6/2015 | Shin | H04L 51/04 726/26 |

FOREIGN PATENT DOCUMENTS

| | | |
|---|---|---|
| WO | WO 2006/050176 A2 | 5/2006 |
| WO | WO 2008/016535 A2 | 2/2008 |

OTHER PUBLICATIONS

International Search Report and Written Opinion, Application No. PCT/US 2014/036343, dated Sep. 18, 2014.
First Examination Report, New Zealand Application No. 713909, dated Mar. 11, 2016.
Canadian Office Action, Canadian Application No. 2,909,965, dated Aug. 26, 2016.

* cited by examiner

4137 N.L.

Motrin (400 mg) q 6 hrs, PRN
Vicodin (5/750 mg) q 4-6 hrs, PRN
Zofran (4mg) q 8 hrs, PRN

| History | | |
|---|---|---|
| Vicodin | 13:00 | 9/14/11 |
| Motrin | 11:00 | 9/14/11 |
| Zofran | 10:00 | 9/14/11 |
| Vicodin | 23:00 | 9/13/11 |
| Motrin | 18:00 | 9/13/11 |

Phonebook | Pharmacy | Worklist | Staff Assist

| Wednesday September 14, 2011 12:53 PM | | | Nurse: Ann M. Tech: Lisa G. Doctor: Dr. Halloway | |
|---|---|---|---|---|
| Main Menu | | | | |
| Back | | My Meals | | |
| Tonight Dinner | Tomorrow Breakfast | | Tomorrow Lunch | Tom |
| Entree Spaghetti and Meatballs Side Beef Barley Soup Beverage Cranberry Juice | Entree Cereal Oatmeal Eggs and Sausage Side Fruit Cup Biscuit Beverage Decaf Coffee Tea Orange Juice | ○○○ ○○ ○○○ | Entree Meatloaf and Potatoes Vegetarian Lasagna Chicken Caesar Salad Side Beef Barley Soup Side Salad Beverage Decaf Coffee Tea Cranberry Juice | Ent Sp M Ve Sid Be Si Bev De Te Cr ○○○ ○○ ○○○ |
| Edit Order | Place Order | | Place Order | |

PATIENT DEVICE FOR ADVANCED PATIENT COMMUNICATION

CROSS-REFERENCE TO RELATED APPLICATIONS

The present application is a divisional of co-pending U.S. patent application Ser. No. 13/460,175 filed on Apr. 30, 2012, which is a continuation-in-part of U.S. patent application Ser. No. 11/778,974 filed on Jul. 17, 2007, which claims the benefit of and priority to U.S. Provisional Patent Application No. 60/831,235 entitled "Advanced Patient Communication System (APaCS)" filed on Jul. 17, 2006, each of which is hereby incorporated by reference. U.S. patent application Ser. No. 13/460,175 also claims the benefit of and priority to U.S. Provisional Patent Application 61/568,073 entitled "Advanced Patient Nurse Call Device" filed on Dec. 7, 2011, which is hereby incorporated by reference.

STATEMENT OF GOVERNMENT RIGHTS

This invention was made with government support under Federal Grant Number 1R41MD006149-01 awarded by the National Institutes of Health, Institute for Minorities and Health Disparities. The government has certain rights in the invention.

TECHNICAL FIELD

The field of the invention relates generally to computer systems and more particularly relates to a patient device for advanced patient communication and healthcare provider communication. More particularly, the present system is in the technical field of nurse call systems.

BACKGROUND

Characteristic of cardiothoracic surgery is the post-operative patient who is sent to the Intensive Care Unit (ICU) intubated due to respiratory requirements. Approximately half of these patients are extubated within their first twenty-four post-operative hours. In most cases these patients are extubated within the first three days. There are some, however, who remain intubated for a significant length of time. When a surgeon identifies a patient who requires intubation longer than seven days, the surgeon will usually decide to perform a tracheotomy on that patient. The breathing support tube enters the trachea rather than entering the mouth for the trached patient. Communication for a intubated or trached patient is minimal due to the inability to speak resulting in the patient, hospital staff and loved ones resorting to the reading of lips, nodding of heads and squeezing of hands to communicate.

Without effective communication, the intubated or trached patient may not receive the standard of care he or she would otherwise receive had he or she been able to effectively communicate. The lack of communication also creates unnecessary levels of anxiety which the patient must endure. Nurses and hospital staff ask many questions from the patient pertaining to their prognosis and progress which may never get fully or even adequately answered. A doctor or nurse is not able to treat a symptom which they know little or nothing about. In addition, other problems arise due to the insufficient communication from the patient. Localized areas of pain are often misdiagnosed, resulting in over-medication generally or the medication of an area which is not the source of pain. Proper and essential treatment given in an adequate and timely manner will help resolve or prevent many post-operative complications and decrease the patient's length of stay in the hospital. This begins with providing the patient a clear and precise means of communication.

Another problem exists in that currently patients are subjected to pushing a button or call light, which turns on a light in the hallway at the doorway to their room. Nurses have no way of identifying whether the patient's need is urgent or non-urgent. Additionally, the nurse is unable to prepare him/herself for the need appropriately before entering the room. Instead, the nurse must go to the patient's room, be informed of the problem or need and then leave the patient's room and retrieve whatever resources are necessary for the nurse to fulfill the patient's need or request. This is extremely time-consuming, wastes precious hospital resources, and can delay meeting the needs of a patient. This problem can be detrimental to the patient when the need is of an urgent matter. Unless the patient can scream loud enough to be heard from wherever help may be, the patient is subjected to wait until someone responds to a common light at the patient's doorway.

Moreover, current systems lack a patient-centric device for the bedside interface (e.g., pillow speaker); and, only a few nurse call systems provide an opportunity for patients to convey specific messages directly to their assigned providers.

Furthermore, eighty percent of hospitals care for patients with limited English proficiency (LEP) on a regular basis, and despite advancements in the profession of healthcare interpreting and translation services (also referred to as Language Access Services), patients with language barriers are often left without an effective means to communicate with their providers. While best practice, clinical ethics and legal and regulatory guidelines recommend the use of professional interpreters for all healthcare encounters, logistics and resource capacity make this prohibitive. Reasons cited by hospital staff for not using professional interpreters include: resources available to bridge the language barrier are not user friendly; resources are not easily accessible; and staff are unaware of the resource and have not been trained. Despite these disadvantages, nurse call systems do not provide a means for LEP patients to generate a nurse call request in the patient's preferred language.

Accordingly, it has been estimated that inefficient communication costs U.S. hospitals more than $12 billion annually or $4 million for each 500 bed hospital. In summary, nurse call systems have been the primary means for hospitalized patients to initiate an encounter from the bedside. However, these nurse call patient requests range in urgency, are not differentiated based on skill-set required to fulfill the patient request, and are not equitable for LEP patients. Further, these shortcomings prohibit effective communication with LEP patients and can contribute to poor outcomes relative to their English-speaking counterparts.

SUMMARY

A method and system for advanced patient communication are disclosed. According to one embodiment, a computer-implemented method comprises providing a patient communication device through which a patient communicates a first message from a hospital bed. The first message is received at a health care provider device. The first message is processed to identify an urgency level of the message. One or more additional messages are generated based on the first message. The one or more additional messages are transmitted to specific health care provider devices of specific health care providers who are expected to respond to the patient.

A patient communication device for advanced patient communication is disclosed. According to one embodiment, a patient communication device comprises a selection input mechanism for generating a message on a display, the message reflecting a patient request and an urgency level associated with the patient request. The selection input mechanism includes one or more of a button, keyboard and a touch screen. Further, the patient communication device includes a transmitter for transmitting the message to a central processing server and a status indicator on the display, the status indicator representing a transmission status associated with the message.

The present system also disclosed a solution that leverages an advanced pillow speaker and receiving devices seeking to achieve immediate transparency for care providers of what patients need when pressing the call button, as well as optimal efficiency in nursing by routing the need to the best provider based on the context of the specific message and the qualified skill necessary to fulfill the request or perform the task being requested.

The above and other preferred features, including various novel details of implementation and combination of elements, will now be more particularly described with reference to the accompanying drawings and pointed out in the claims. It will be understood that the particular methods and systems described herein are shown by way of illustration only and not as limitations. As will be understood by those skilled in the art, the principles and features described herein may be employed in various and numerous embodiments without departing from the scope of the teachings herein.

BRIEF DESCRIPTION OF THE DRAWINGS

The accompanying drawings, which are included as part of the present specification, illustrate the presently preferred embodiment of the present invention and together with the general description given above and the detailed description of the preferred embodiment given below serve to explain and teach the principles of the present invention.

Figure 5H:
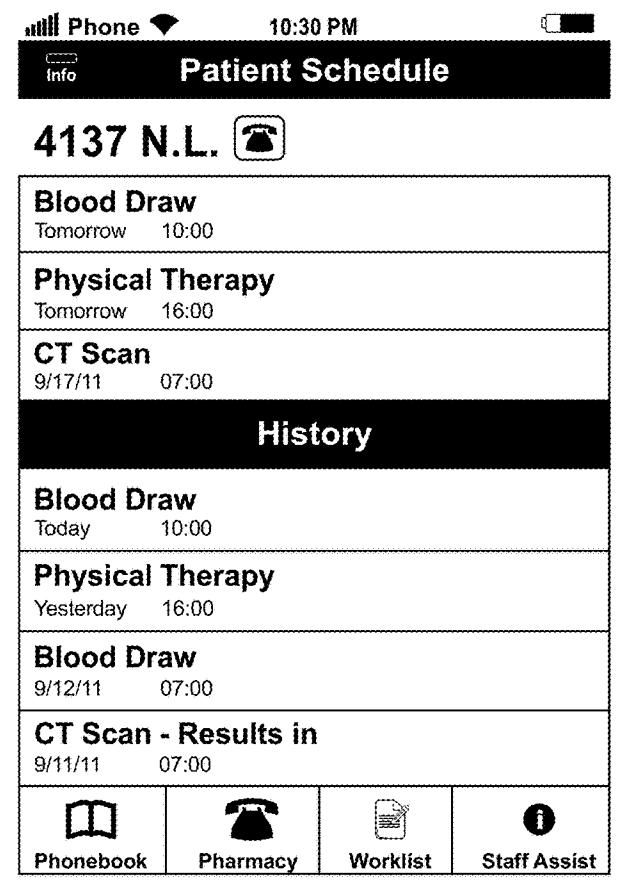

FIGS. 5A-5I are exemplary care provider view interfaces within a phone application that displays nurse call activity and other pertinent patient information on handheld devices, according to one embodiment.

FIG. 6 is an exemplary interface of a nursing station whiteboard that displays the nurse call activity by provider, patient room, number of requests queued by provider and context of each call request, according to one embodiment.

FIGS. 8 A-D illustrate exemplary sub-categorical interfaces within an exemplary advanced pillow speaker, according to one embodiment.

Figure 1:
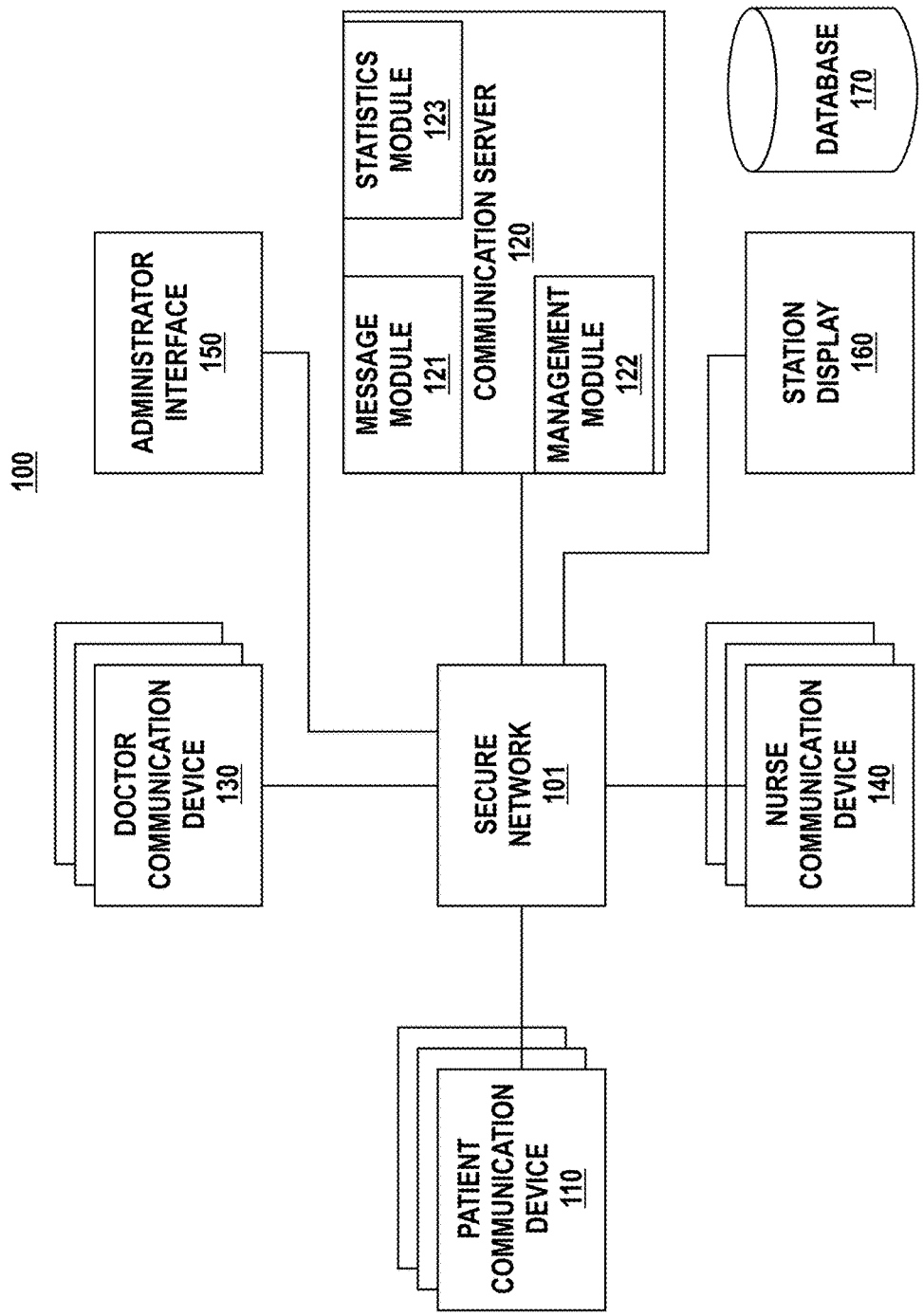
FIG. 1 illustrates a block diagram of an exemplary system for advanced patient communications, according to one embodiment.

It should be noted that the figures are not necessarily drawn to scale and that elements of similar structures or functions are generally represented by like reference numerals for illustrative purposes throughout the figures. It also should be noted that the figures are only intended to facilitate the description of the various embodiments.

DETAILED DESCRIPTION

A method and system for advanced patient communication are disclosed. According to one embodiment, a computer-implemented method comprises providing a patient communication device through which a patient communicates a first message from a hospital bed. The first message may be transmitted directly to a health care provider device(s) and/or may be received at a central processing server. The first message may be processed to identify urgency level of the message and/or appropriate destination(s) for the request. The first message may also originate from a healthcare provider or a central processing server. One or more additional messages are generated based on the first message. The one or more additional messages are transmitted to devices of specific health care providers who are expected to respond to the patient and may also be transmitted back to the patient.

In the following description, for purposes of explanation, specific nomenclature is set forth to provide a thorough understanding of the various inventive concepts disclosed herein. However, it will be apparent to one skilled in the art that these specific details are not required in order to practice the various inventive concepts disclosed herein.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, USB drives, internal or external hard disk drives, floppy disks, optical disks, CD-ROMs, magnetic-optical disks, read-only memories, random access memories, EPROMs, EEPROMs, magnetic or optical cards, or any type of media suitable for storing electronic instructions, and each coupled to a computer system bus.

The methods presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

FIG. 1 illustrates a block diagram of an exemplary system 100 for advanced patient communications, according to one embodiment. System 100 includes a number of patient communication devices 110. In the context of a hospital, each patient's bed includes a patient communication device 110 that may be an electronic bedside, flat screen monitor. One embodiment can be attached to a waterproof sealed keyboard. Additional input devices may be used for patients with limited or minimal movement. These patient communication devices 110 may have a sealed push button, lever, jog dial, or a combination of these input devices. According to another embodiment, the input device is a touch pad screen.

The patient communication device 110 may also have a card reader attached to read a card carried by the staff to indicate when they have responded to a call. In this respect, a nurse or other care provider can carry a card (card with a magnetic stripe, proximity, smart card) and swipe it. This method would serve to prevent the patient from accidentally clearing the request, and reduce the interaction with the pager, which might be cumbersome and time-consuming, used more often when requests require specific feedback. Monitoring-only stations configured in this manner could be placed throughout the floor for "fast response".

One embodiment of the patient communication device 110 allows its monitor to sit directly on a flat surface, such as a bedside table. In another embodiment, the monitor is attached to a swiveling arm extending from the wall so that it can be extended to various distances from the wall and heights from the floor, thus adapting to the patient's position.

In one embodiment, the patient communication device 110 allows electronic communication of the physical and emotional status of the patient. Words and phrases may be selected in the display of device 110, such as "I AM: HOT/COLD, THIRSTY, HUNGRY, TIRED, LIGHT-HEADED, NAUSEOUS, ANXIOUS, NERVOUS, BETTER, WORSE, DIRTY/WET, HAPPY/SAD". Additional screens and prompts allow the patient to select words and phrases such as "I WANT: WATER/ICE, CALL LIGHT/TV, TO TURN, LEFT/RIGHT, TO LIE DOWN, A BLANKET, TO SLEEP, BATH/SHAMPOO, A BEDPAN, TO CLEAN MY MOUTH/TEETH/FACE/HANDS." Words such as "YES/NO, EXPLAIN, CALL, NURSE, SUCTION, LOTION, GLASSES, FAMILY, INSURANCE, LIGHT, ON/OFF, WHEN?, WHY?, WHERE?, WHO?, HOW?, WHAT?" are listed for selection if the health care provider verbally questions the patient, and the patient responds through device 110.

According to one embodiment, patient communicator device 110 also provides a grid imprinted with individual letters of the alphabet and the numbers 0-9. Universal characters and symbols may also be used to select text in lieu of keyboard input. The device 110 may also provide a screen that displays an image of the anterior body picture with the word "FRONT" underneath, and the posterior body picture with the word "BACK" underneath it. Between the two bodies are descriptive words to express physical experiences relating to any part of the human body. These include the words and phrases: "THIS PART OF MY BODY: ITCHES, ACHES, STINGS, CAN'T MOVE, CAN'T MOVE, HURTS, BURNS, CRAMPS, THROBS, IS NUMB, PAIN MEDICINE". In addition, at the bottom, a nationally established pain scale lists: "PAIN SCALE: 012345678910" and the following words indicating a correlation with the degree of pain: "NO PAIN, SLIGHT PAIN, MODERATE PAIN, SEVERE PAIN, WORST PAIN".

According to one embodiment, each word, phrase and symbol listed on the above mentioned screen layouts activates a computer operated voice dictation of the messages through a built-in speaker when touched. The patient communication device 110 has several menu options including choice of language, pediatric variations, and voice style options such as male or female and adult or child computerized voices. The patient communication device 110 may also be used by a doctor or nurse as a chart, or to display an electronic form of the patient's chart. Additionally, the patient communication device 110 can be used by the doctor or nurse to order procedures, consults, medications, and indicate that treatments, consultations, examinations, and other procedures have been completed.

According to one embodiment, patient communication device 110 is a menu driven touch-screen device. It includes a menu that is a touch-screen keyboard for manual text entry. Patient communication device 110 may either be wireless or have a wire connection to the hospital network. Patient communication device 110 works with a variety of languages and is capable of input and output translation between them. According to one embodiment, patients check medications, schedules, and diagnoses in addition to other information about themselves directly through the patient communication device 110. Patient communication device 110 includes the following capabilities:

a. Panic button located on patient communication device 110, simple to use but hard to accidentally trigger
   i. Goes directly to assigned nurse or team of nurses and communication server 120 b. Patient communication device 110 may have an integrated speaker and microphone
   i. Patient can send voice messages to nurse. Message automatically goes to nurse or team of nurses assigned to patient. A time stamp and bed number are automatically attached to the voice message. Voice recognition may convert voice to text and/or translate message.
   ii. Patient can respond to voice messages sent from nurse, doctor, and base station. Speech recognition may convert voice to text and/or translate message.
   iii. Patient can hear voice messages sent from nurse, doctor, and base station. Voice recognition may convert voice to text and/or translate message.
   iv. Option to use the microphone and speaker to enable use of a patient communication device 110 as a mobile phone for patient to make and receive calls through hospital network and/or an outside cellular carrier.
      1. Board may have ability to accept SIM card c. Adjustable ring and vibration alert for message waiting d. Read self-information
   i. Patient can walk through menus that display select elements of their own patient_data e. Make a request (goes to assigned nurse or team of nurses and monitored by communication server 120)
   i. Automatic return address and timestamp added to request
   ii. Menu of requests (i.e., water, medication, blanket . . . )
      1. Option to hand enter special requests
   iii. Menu of urgency (i.e., ASAP, 5 min, 15 min, in next hour, today, information only—no response needed)

f. Read response to request g. Read a reminder/announcement sent from nurse communication device 140, doctor communication device 130, or communication server 120 (no response requested)

h. Read an informational request sent from nurse communication device 140, doctor communication device 130, or communication server 120 i. Respond to an informational request from nurse communication device 140, doctor communication device 130, or communication server 120
   i. Automatic return address and timestamp added to response
   ii. Menu of typical responses
   iii. Option to hand enter response j. Optional capabilities
   i. Read/send text messages to cell phones (optional, may be fee based)
   ii. Games may be ported to the boards
   iii. May have internet capability System 100 also includes a number of healthcare provider communication devices, including doctor communication devices 130 and nurse communication devices 140. Doctor communication device 130 and nurse communication device 140 allow for communication with the patient communication device 110, so that nurses and doctors may respond to requests from the patient for treatment, etc. According to one embodiment, doctor and nurse communication devices 130, 140 take the form of interactive pagers [patient-healthcare provider paging system], a central communication workstation or PC, PDAs, tablet PCs, videophones, laptops, smart phones, mobile phones, game devices such as the PSP® manufactured by Sony Electronics, multimedia devices such as iPods® and iPhones® manufactured by Apple Computers of Cupertino, Calif., or similar devices. Devices 130 and 140 may be fully web enabled, such that the interface is provided through a web browser. In an alternate embodiment, devices 130 and 140 execute software applications to perform the present methods.

The nurse 140 and doctor 130 communication devices have several menu options including choice of language, pediatric variations, and voice style options such as male or female and adult or child computerized voices. The nurse 140 and doctor communication devices 130 may also be used as a chart, or to display an electronic form of the patient's chart. Additionally, the nurse 140 and doctor communication devices 130 can be used by the doctor or nurse to order procedures, consults, medications, and indicate that treatments, consultations, examinations, and other procedures have been completed.

According to one embodiment, the doctor communication device 130 is a wireless device that may work through a wireless provider, the hospital network, and/or a standalone system. It works with a variety of languages and is capable of input and output translation between them. Doctor communication device 130 includes the following capabilities:

a. Doctor communication device 130 may have an integrated speaker and microphone
   i. Doctor can send voice messages to any patient, nurse, other doctor, or base station. Message automatically has a time stamp, doctor name and doctor ID linked to it.
   ii. Doctor can respond to voice messages sent from patient, nurse, another doctor, and base station
   iii. Doctor can hear voice messages sent from patient, nurse, doctor, and base station
   iv. Option to use the microphone and speaker to enable use of doctor communication device 130 as a mobile phone for doctor to make and receive calls through hospital network and/or an outside cellular carrier
      1. Pager may have ability to accept SIM card
b. Adjustable ring and vibration alert for message waiting
   i. Different alert for ASAP Requests and Panic signal from patient communication device 110
c. Read nursing_staff_assignments
   i. Can also search by zone, sub-zone, nurse name or nurse ID
d. Read patient_data for any patient
   i. Choice of multiple look-up fields such as patient name, patient ID, bed number, doctor ID . . .
e. Change/update patient_data fields (some may be reserved)
   i. Choice of multiple look-up fields such as patient name, patient ID, bed number, doctor ID . . .
f. Monitor patient/nurse communications
g. Send a reminder/announcement to a patient
   i. Automatic return address and timestamp added
   ii. Choice of multiple look-up fields such as patient name, patient ID, bed number, doctor ID . . .
   iii. Can send to groups of patients (i.e., all maternity, all patients of a given doctor)
   iv. Menu of typical reminders and announcements
      1. Option to hand enter a reminder or announcement
h. Send an informational request
   i. Automatic return address and timestamp added to request
   ii. Choice of multiple look-up fields such as patient name, patient ID, bed number, doctor ID . . .
   iii. Can send to groups of patients (i.e., all maternity, all patients of a given doctor)
   iv. Menu of typical information requests
      1. Each request is associated with a menu of typical responses for patient
   v. Option to hand enter a request
i. Read response to an informational request from patient
   i. Menu of typical responses
   ii. Option to hand enter response
j. Send and receive text messages to/from another nurse communication device 140, doctor communication device 130, communication server 120, and cell phones.
   i. Options to reject messages from a "reject" list of phone numbers or only accept messages from an "accept" list
   ii. Can search for addressee zone, sub-zone, nurse name, nurse ID, etc. or by phonebook of previous addressees
   iii. Menu of common messages
      1. Option to hand enter message
   iv. Expected response
      1. Please call
      2. Return reply
      3. Please page
      4. Please come
      5. FYI—no response needed
      6. Option to hand enter expected response
   v. Please reply by:
      1. ASAP
      2. Within 5 min
      3. Within 10 min
      4. Within 15 min
      5. Within 1 hour
      6. Within 4 hours
      7. Option to hand enter requested reply time
k. Doctor communication device 130 may have an integrated camera and/or ability to connect to a camera
   i. Doctor can send images to any patient, nurse, other doctor, or base station. Message automatically has a time stamp, doctor name and doctor ID linked to it.
   ii. Doctor can respond to images sent from patient, nurse, another doctor, and base station
   iii. Doctor can view images sent from patient, nurse, doctor, and base station According to one embodiment, the nurse communication device 140 is a wireless device that may work through a wireless provider, the hospital network, or a standalone system. It works with a variety of languages and is capable of input and output translation between them. Nurses send information requests and reminders such as "take medications" directly to patient communication device 110. Nurse communication device 140 includes the following capabilities:

a. Nurse communication device 140 may have an integrated speaker and microphone
   i. Nurse can send voice messages to any patient, other nurse, doctor, or base station. Message automatically has a time stamp, nurse name and nurse ID linked to it.
   ii. Nurse can respond to voice messages sent from patient, other nurse, doctor, and base station
   iii. Nurse can hear voice messages sent from patient, nurse, doctor, and base station
   iv. Option to use the microphone and speaker to enable use of nurse communication device 140 as a mobile phone for nurse to make and receive calls through hospital network and/or an outside cellular carrier
      1. Pager may have ability to accept SIM card
b. Adjustable ring and vibration alert for message waiting
   i. For example, different alert for ASAP Requests and Panic signal from patient communication device 110
c. Read nursing_staff_assignments
   i. 1-touch for self-assignment
   ii. Can also search by zone, sub-zone, nurse name or nurse ID
d. Read patient_data for any patient
   i. Choice of multiple look-up fields such as patient name, patient ID, bed number, doctor ID . . .
e. Change/update patient_data fields (some may be reserved)
   i. Choice of multiple look-up fields such as patient name, patient ID, bed number, doctor ID . . .
f. Read a patient request
g. Respond to a patient request with action or with verbally/text response
   i. Responded requests are flagged to notify other care providers that the patient need is being addressed and for that highlighted signal to appear on all pagers that received that message. These requests have the return address of the responding healthcare provider and a timestamp added.
   ii. Automatic return address and timestamp added to request
   iii. Menu of 1 touch replies
      1. Will do
      2. Will do, but with some delay
         a. Menu of delay times (i.e., uncertain, 5 min, 10 min . . . )
      3. Cannot do
      4. See text
   iv. Optional: can add personal message in reply
   v. Do not need electronic response to ASAP request and panic button
h. Set a timed reminder for request
   i. Delayed requests are highlighted as on-hold to notify other care providers that a healthcare provider intends to respond to the request. These highlighted signals appear on all pagers that received that message with the return address of the responding healthcare provider and a time of reminder added.
i. Send a reminder/announcement to a patient
   i. Automatic return address and timestamp added
   ii. Choice of multiple look-up fields such as patient name, patient ID, bed number, doctor ID . . .
   iii. Can send to groups of patients (i.e., all maternity, all patients of a given doctor)
   iv. Menu of typical reminders and announcements
      1. Option to hand enter a reminder or announcement
j. Send an informational request
   i. Automatic return address and timestamp added to request
   ii. Choice of multiple look-up fields such as patient name, patient ID, bed number, doctor ID . . .
   iii. Can send to groups of patients (i.e., all maternity, all patients of a given doctor)
   iv. Menu of typical information requests
      1. Each request is associated with a menu of typical responses for patient
   v. Option to hand enter a request
k. Read response to an informational request from patient
   i. Menu of typical responses
   ii. Option to hand enter response
l. Forward the request to another nurse
   i. Works similar to assigning patients to another nurse, but there are no return address.
m. Assign from 1 to all patients to another nurse communication device 140
   i. Select assignee by zone, sub-zone, nurse name, nurse ID, or other field in nursing_staff_assignments
   ii. Automatically identifies forwarding nurse information (RTN)
   iii. Ability to include a text message to assignee
      1. 1 touch list of common messages
      2. Optional: can add personal message
   iv. Automatically notifies assignee
      1. Requires response confirmation/rejection (simple 1 touch)
   v. Notifies forwarding nurse after confirmation/rejection
n. Respond to an assignment request
   i. 1 touch "Yes/No" response
   ii. "Yes" updates fields in patient_data and nursing_staff_assignments
   iii. Option to hand enter comment to add to response
o. Re-assign, same as "Assign" except keeps original nurse return information (RTN) and notifies both last responsible and originally assigned nurse of affirmative response from assignee
   i. Select assignee by zone, sub-zone, nurse name or nurse ID
   ii. Saves original forwarding nurse information (RTN)
   iii. Ability to include a text message to assignee
      1. 1 touch list of common messages
      2. Optional: can add personal message
   iv. Automatically notifies assignee
      1. Requires response confirmation/rejection (simple 1 touch)
   v. Notifies both re-forwarding nurse and original forwarding nurse after positive confirmation
   vi. Only notify re-forwarding nurse if request is rejected p. Return, for original nurse to return from 1 to all forwarded patients to self 1-touch option for returning all forwarded patients
   i. Automatically notifies assignee
      1. No confirmation required
   ii. Updates fields in patient_data and nursing_staff_assignments
q. Send and receive text messages to/from another nurse communication device 140, doctor communication device 130, communication server 120, and cell phones
   i. Options to reject messages from a "reject" list of phone numbers or only accept messages from an "accept" list
   ii. Can search for addressee zone, sub-zone, nurse name, nurse ID, etc. or by phonebook of previous addressees
   iii. Menu of common messages
      1. Option to hand enter message
   iv. Expected response
      1. Please call
      2. Return reply
      3. Please page
      4. Please come
      5. FYI—no response needed
      6. Option to hand enter expected response
   v. Please reply by:
      1. ASAP
      2. Within 5 min
      3. Within 10 min
      4. Within 15 min
      5. Within 1 hour
      6. Within 4 hours
      7. Option to hand enter requested reply time
r. Nurse communication device 130 may have an integrated camera and/or ability to connect to a camera
   i. Nurse can send images to any patient, nurse, doctor, or base station. Message automatically has a time stamp, doctor name and doctor ID linked to it.
   ii. Nurse can respond to images sent from patient, nurse, doctor, and base station
   iii. Nurse can view images sent from patient, nurse, doctor, and base station Communication server 120 of system 100 includes message module 121 for sending messages to patient communication devices 110, such as e-mails, pages, SMS text messages, MMS messages, data files, etc. Communication server 120 also has a management module 122 that coordinates the exchange of messages between devices 110, 130, and 140, administrator interface 150 and the treatment of patients. Management module 122 also facilitates the prioritization of patient calls. For example, in addition to addressing safety issues related to unrecognized emergent needs, to improve the delivery of in-patient healthcare, patient needs are prioritized relative to their urgency. According to the characteristic of the need, various care providers are qualified for helping the patient. Nurses may then manage their duties from a priority standpoint without having to address the many non-urgent needs that can be easily met by a hospital assistant or nursing assistant. In this respect, having a nurse respond to a call light that demonstrates a need, which a non-skilled professional can satisfy, consumes limited hospital energy and resources that should be directed elsewhere. The management module 122 provides prompts to patients, nurses, doctors, and staff to ensure that protocols are maintained for the treatment of patients. The protocols may conform to industry wide standards, or hospital and caregiver specific requirements.

Communications server 120 also includes a statistics module 123 that collects and analyzes information relating to the treatment of patients. For example, statistics module 123 analyzes data to track specific patient problems, analyzing prioritizing of patient calls, patient safety, hospital resources, patient satisfaction and timeliness of meeting requests.

Communication server 120 may be a web server that uses any one of a number of protocols and/or applications including HyperText Transfer Protocol (HTTP), File Transfer Protocol (FTP), Internet Relay Chat (IRC), etc., via a TCP/IP connection (not shown in this view) or other similar connection protocols. The operating system may be Windows®, Linux®, SUN Solaris®, Mac OS®, Tiger, or other similar operating system. In one embodiment, the MMSW server 130 is a dedicated server. It uses processing logic, tools and databases and is built using a combination of technologies such as those from Apache Software ( ) such as Tomcat® servers; Java based technologies such as J2EE, EJB, JBOSS, JDBC; and/or databases such as MySQL.

According to one embodiment, the communications server 120 may work through a wireless provider, the hospital network, or a standalone system. It works with a variety of languages and provides input and output translation between them. Communication server 120 has the following capabilities:
   a. Communication server 120 may have an integrated speaker and microphone or may be linked into the telephone at the base station
      i. Base station can send voice messages to any patient, doctor, or nurse. Message automatically has a time stamp, operator name, and operator ID linked to it.
      ii. Base station can respond to voice messages sent from patient, nurse, and doctor
      iii. Base station can hear voice messages sent from patient, nurse, and doctor
   b. Adjustable alert for message waiting
      i. Different alert for ASAP Requests and Panic signal from patient communication device 110
   c. Set up and change menu options for all other devices
   d. Assign nurses
      i. Automatically updates nursing_staff_assignments
      ii. Automatically sends text message to affected nurse communication devices 140
   e. Read nursing_staff_assignments
      i. Can search by zone, sub-zone, nurse name, nurse ID, etc.
   f. Enter/remove patient into/from database
   g. Read/change/update patient_data for any patient
      i. Choice of multiple look-up fields such as patient name, patient ID, bed number, doctor ID . . .
   h. Monitor patient/nurse communications
   i. Send a reminder/announcement to a patient
      i. Automatic return address and timestamp added
      ii. Choice of multiple look-up fields such as patient name, patient ID, bed number, doctor ID . . .
      iii. Can send to groups of patients (i.e., all maternity, all patients of a given doctor)
      iv. Menu of typical reminders and announcements
         1. Option to hand enter a reminder or announcement
   j. Send an informational request
      i. Automatic return address and timestamp added to request
      ii. Choice of multiple look-up fields such as patient name, patient ID, bed number, doctor ID . . .
      iii. Can send to groups of patients (i.e., all maternity, all patients of a given doctor)

iv. Menu of typical information requests
  1. Each request is associated with a menu of typical responses for patient
v. Option to hand enter a request
k. Read response to an informational request from patient
  i. Menu of typical responses
  ii. Option to hand enter response
l. Send and receive text messages and image files (such as in jpeg or tiff format) to/from nurse communication device 140, doctor communication device 130, and cell phones.
  i. Options to reject messages from a "reject" list of phone numbers or only accept messages from an "accept" list
  ii. Can search for addressee zone, sub-zone, nurse name, nurse ID, etc. or by phonebook of previous addressees
  iii. Menu of common messages
    1. Option to hand enter message
  iv. Expected response
    1. Please call
    2. Return reply
    3. Please page
    4. Please come
    5. FYI—no response needed
    6. Option to hand enter expected response
  v. Please reply by:
    1. ASAP
    2. Within 5 min
    3. Within 10 min
    4. Within 15 min
    5. Within 1 hour
    6. Within 4 hours
    7. Option to hand enter requested reply time System 100 includes an administrator interface 150 that allows system configuration and process flow for advanced patient communications. For example, administrator interface 150 may be a touch screen PC that monitors all patients, and receives communications from a patient communication device 110. From the administrator interface 150, messages may be sent to nurse communication device 140 and/or doctor communication device. Through administrator interface 150, an administrator, such as a head nurse, doctor or workflow coordinator may access information relating to patients, as well as each nurse, staff member and doctor. The information may include performance statistics for doctors, nurse, and staff, as well as treatment information for the patient.

A station display 160 allows for the display of patient related information. The display 160 may be located behind a nurse's station such that all nurses, doctors, and staff may see which beds are assigned to patients, nursing and doctor assignments, as well as treatment information if a patient codes and needs immediate attention. The display may also indicate if the patient is alone, with visitors, a doctor, a nurse, staff, or other person. The display may also indicate a status for a treatment process for a particular patient, for example, consult needed by a particular specialist, or medication to be administered by a particular nurse. A station display 160 may also be placed outside a hospital patient room and provide information specific to the particular patient.

A station display 160 allows for a wireless provider, the hospital network, or a standalone system. It is designed to work with a variety of languages and is capable of translation between them. Display may alternate in time between two or more languages and/or may have language adjustment capability. Station display 160 has the following assignments.
  a. Displays fields from nursing_staff_assignments and patient_data
  b. May have multiple displays, multiple windows cycling on each display, or menu-based displays
  c. Displays current patient Panic signal and ASAP request data System 100 includes a database 170 that stores a variety of patient and healthcare provider information. Patient data stored in database 170 includes for each patient:
  a. Name: Patient name
  b. Int: Patient ID number
  c. Text: Primary language
  d. Text: Additional languages
  e. Time: Admit date
  f. Text: Diagnosis
  g. Name: Doctor name
  h. Int: Doctor ID number
  i. Text: Allergies
  j. Emergency Contact
    i. Name: Contact Name
    ii. Int: Contact Telephone number
    iii. Int: Contact Secondary telephone number
    iv. Address: Contact Address
  k. Array:
    i. Text: Medications
  l. Name: Nurse name
  m. Int: Nurse ID number
  n. Name: RTN nurse name (return address for use with forwarding)
  o. Int: RTN nurse ID number (return address for use with forwarding)
  p. Int: Bed number
  q. Text: comments/notes from Nurses and Doctors
  r. Array (for all communication to and from the patient)
    i. Text: Requests and responses The patient data may be searched, accessed and edited in many ways as follows:
  a. From communication server 120—can search by any data field (i.e., doctor, diagnosis . . . )
    i. Enter
    ii. Read
    iii. Update
    iv. Delete
    v. Automatic archive whenever data field is updated
  b. From nurse communication device 140—can search by any data field (i.e., doctor, diagnosis . . . )
    i. Read
    ii. Update (some variables such as patient ID number may be restricted from nurse update)
  c. From patient communication device 110—can only access data for patient assigned to board
    i. Read only (some data may be restricted from view)
  d. From station display 160
    i. Read only (some data may be restricted from view)
  e. From doctor communication device 130—can search by any data field (i.e., doctor, diagnosis . . . )
    i. Read
    ii. Update (some variables such as patient ID number may be restricted from doctor update)

Nursing staff assignments information stored in database 170 includes for each nurse:
- a. Array (for each nurse on duty)
  - i. Name: Nurse name
  - ii. Int: Nurse ID number
  - iii. Nurse Information:
    1. Text: Nurse primary language
    2. Text: Nurse additional languages
    3. Text: Nurse specialties (i.e., x-ray technician)
    4. Optionally more fields
  - iv. Text: Hospital zone assigned (i.e., 3rd floor, maternity . . . )
    1. Text: sub-zone (i.e., 3rd floor/admissions)
  - v. Array (for each of this nurse's patients)
    1. Name: Patient name
    2. Int: Patient ID number
    3. Int: Patient bed number The nurse assignment data (that may change every shift) may be searched, accessed and edited in many ways as follows:
- a. Electronic display of assignments posted at communication server 120
- b. From communication server 120—can search by any data field (i.e., nurse name, patient name . . . )
  - i. Enter
  - ii. Read
  - iii. Update
  - iv. Delete
  - v. Automatic archive whenever data field is updated
- c. From nurse communication device 140—can search by any data field (i.e., nurse name, zone . . . )
  - i. Read nursing_staff_assignments for self or any other nurse
    1. Simple (1 touch) to read nursing_staff_assignments for self
    2. Can search by zone, sub-zone, nurse name, or nurse ID
  - ii. Forwarding (can temporarily re-assign patients to another nurse)
- d. From patient communication device 110—not used by patient communication device 110
- e. From station display 160
  - i. Read only
- f. From doctor communication device 130
  - i. Read only Patient request information stored in database 170 includes for each request:
- a. Header:
  - i. Name: Patient name
  - ii. Int: Patient ID number
  - iii. Text: Diagnosis
  - iv. Name: Doctor name
  - v. Int: Doctor ID number
  - vi. Text: Allergies
  - vii. Array:
    1. Text: Medications
  - viii. Name: Nurse name
  - ix. Int: Nurse ID number
  - x. Name: RTN nurse name (return address for use with forwarding)
  - xi. Int: RTN nurse ID number (return address for use with forwarding)
  - xii. Int: Bed number
- b. Request
  - i. Text: Description of request
  - ii. Text: Urgency of request
- c. Response
  - i. Flag: Pending
  - ii. Flag: In a nurses' queue (reminder set up)
    1. Name: Nurse name
    2. Int: Nurse ID number
    3. Time: Time of reminder
  - iii. Flag: Responded to
    1. Name: Nurse name
    2. Int: Nurse ID number
    3. Time: Time of response The patient request data may be searched, accessed and edited in many ways as follows:
- a. From communication server 120—can search by any data field (i.e., nurse name, patient name . . . )
  - i. Read
  - ii. Update
  - iii. Delete
  - iv. Automatic archive whenever data field is updated or entry is deleted
- b. From nurse communication device 140—default display requests to nurse, but can also search by any data field (i.e., nurse name, zone . . . )
  - i. Read
  - ii. Set a reminder for later
  - iii. Forward to another nurse
  - iv. Highlight as in-progress
  - v. Delete
  - vi. Automatic archive whenever data field is updated or entry is deleted
- c. From patient communication device 110—not used by patient communication device 110
- d. From station display 160
  - i. Read only
- e. From doctor communication device 130—expect to usually be read, not modified
  - i. Set a reminder for later
  - ii. Forward to a different nurse
  - iii. Highlight as in-progress
  - iv. Delete
  - v. Automatic archive whenever data field is updated or entry is deleted One or more of communication devices 110, 130, 140, administration interface 150, communication server 120 and station display 160 may allow network access via a web browser such as Microsoft's Internet Explorer®, Netscape Navigator®, Mozilla Firefox®, or the Safari® browsers that support HTML and JavaScript.

Communication devices 110, 130, 140, administration interface 150, communication server 120 and station display 160 are interconnected by secure network 101. According to one embodiment, network 101 is described as being the Internet, alternatively, the network 101 may be a Wide Area Network (WAN), a Local Area Network (LAN), or any other system of interconnections enabling two or more devices to exchange information. Further, the network 101 may include a wireless network, such that one or more of devices 110, 130, 140, administration interface 150, communication server 120 and station display 160 may be wireless devices.

System 100 may also include other supporting computing software and hardware, for example, additional website servers, databases, computers, and user interface servers.

Figure 2:
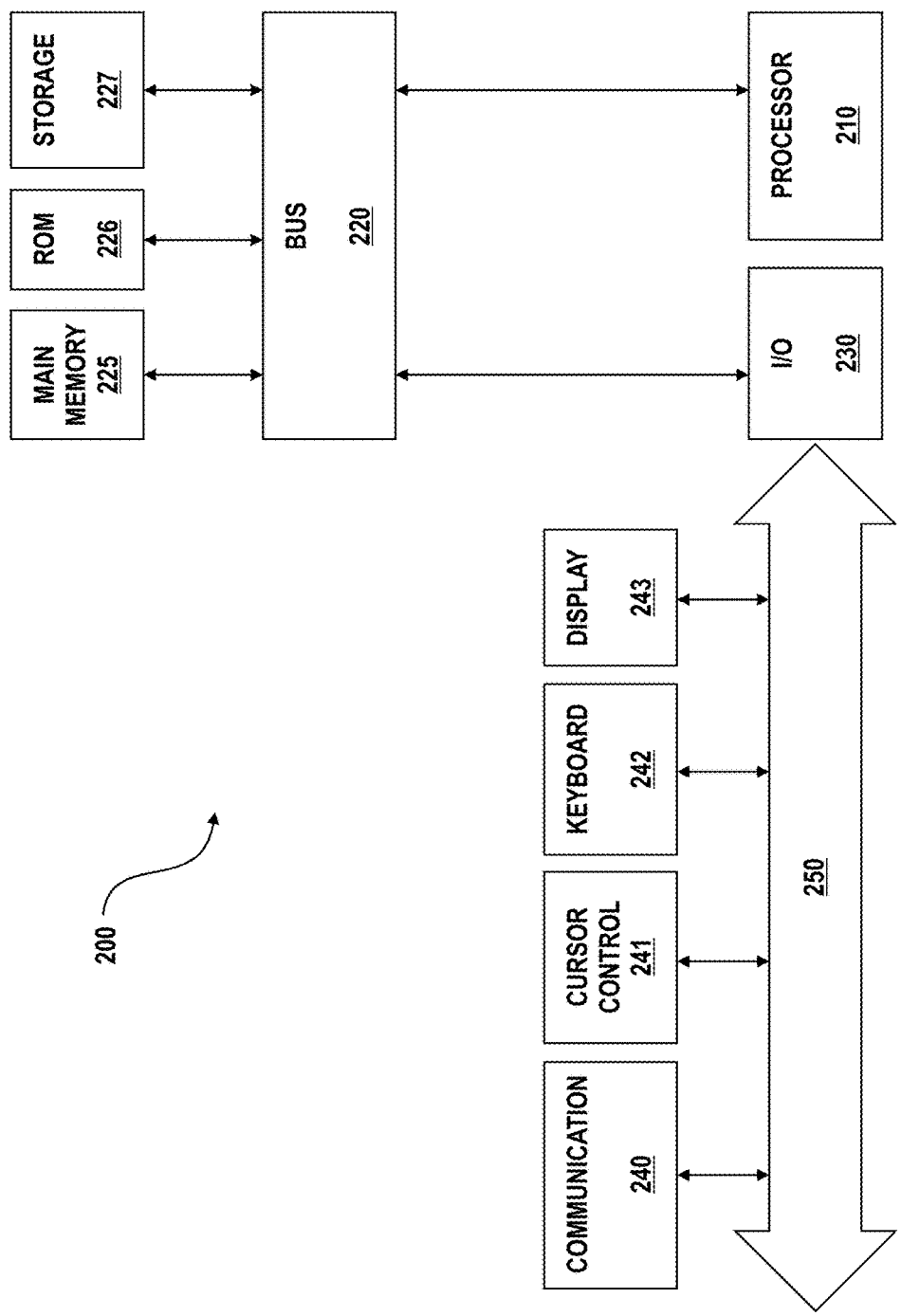
FIG. 2 illustrates an exemplary computer architecture for use with the present system, according to one embodiment.

FIG. 2 illustrates an exemplary computer architecture for use with the present system, according to one embodiment.

Computer architecture 200 can be used to implement a devices 110, 130, 140, administration interface 150, and communication server 120 of FIG. 1. One embodiment of architecture 200 comprises a system bus 220 for communicating information, and a processor 210 coupled to bus 220 for processing information. Architecture 200 further comprises a random access memory (RAM) or other dynamic storage device 225 (referred to herein as main memory), coupled to bus 220 for storing information and instructions to be executed by processor 210. Main memory 225 also may be used for storing temporary variables or other intermediate information during execution of instructions by processor 210. Architecture 200 also may include a read only memory (ROM) and/or other static storage device 226 coupled to bus 220 for storing static information and instructions used by processor 210.

A data storage device 227 such as a magnetic disk or optical disc and its corresponding drive may also be coupled to computer system 200 for storing information and instructions. Architecture 200 can also be coupled to a second I/O bus 250 via an I/O interface 230. A plurality of I/O devices may be coupled to I/O bus 250, including a display device 243, an input device (e.g., an alphanumeric input device 242 and/or a cursor control device 241). For example, web pages rendered by MMSW server 130 and related information may be presented to the user on the display device 243.

The communication device 240 allows for access to other computers (servers or clients) via a network. The communication device 240 may comprise a modem, a network interface card, a wireless network interface or other well-known interface device, such as those used for coupling to Ethernet, token ring, or other types of networks.

Figure 3:
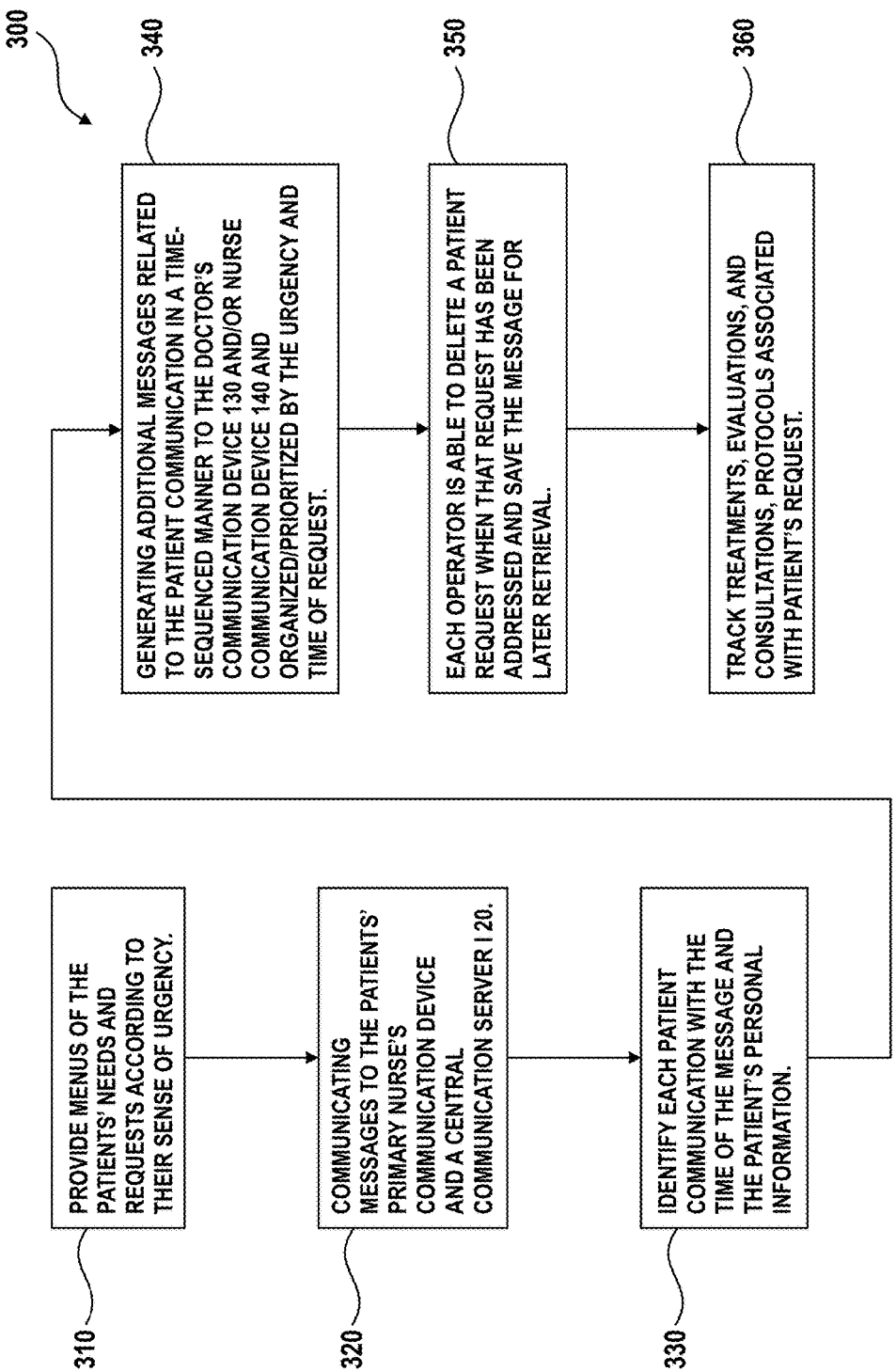
FIG. 3 illustrates an exemplary communications process, according to one embodiment.

FIG. 3 illustrates an exemplary communications process 300, according to one embodiment. System 100 directs the patient through the use of the patient communication device 110 that provides menus of the patients' needs and requests according to their sense of urgency. (310) In this same respect, the patient's needs—as they are selected or typed out—are messaged to the patient's healthcare providers on their doctor's communication device 130 and/or nurse communication device 140 and a central communication server 120. (320) One embodiment allows the patient's primary nurse to be able to receive all messages from his/her patient(s). Furthermore, those specific needs, which are appropriate for a non-licensed healthcare professional, such as a hospital assistant or nurse assistant, are messaged accordingly.

The time of the message in addition to the patient's personal information identifies each patient request/communication. (330) As each request is made, the patient's literal request or need is messaged in a time-sequenced manner to the doctor's communication device 130 and/or nurse communication device 140 and organized/prioritized by urgency and time of request. (340)

One embodiment allows for either one-way or two-way text or voice communication between the patient care staff or the patient care staff and the patient. According to one embodiment, a voice communication system uses a speech recognition system which deciphers verbal messages and submits them either in voice or text. In such a way, the doctor's communication device 130 and/or nurse communication device 140 provides text of voice input or actually transmit the voice into an audible speaker. The patient communication device 110 may also allow the patient to hear the patient care staff speaking to them. This would best serve patients who cannot read and can only use their voice to communicate or for patients for whom speaking and hearing is the most convenient method of communicating.

When using system 100, each operator is able to delete a patient request when that request has been addressed and save the message for later retrieval. (350) One embodiment allows the operator to program all saved messages for timed reminders at the time the message is saved. Additionally, one embodiment of the system 100 allows multiple communication devices to interact with one another so that a healthcare team involving nurses and their assistants may be able to request assistance from one another if warranted by the situation.

After messaging all required care givers, the present system tracks any treatments, evaluations, and consultations, to ensure that protocols associated with a patient request are followed. (360) The system 100 generates additional messages, stores data in the database 170 and tracks the progress of the healthcare providers until the patient's request is complete.

System 100 facilitates the identification of a patient need being addressed. Since multiple people may receive the same patient request on their communication device, the care provider assisting with that specific need may highlight the message with a function key on the communication device 110, 130, or 140 to notify other care providers that the patient's need is being addressed and for that highlighted signal to appear on all devices 130, 140 that received that message. This eliminates two or more people going to the same patient at the same time for the same need. It also allows all those who have been contacted to see which patient needs/requests remain unaddressed. In this respect, system 100 provides an efficient way for communication between patients and their care providers and amongst the care providers themselves.

In addition to patient messages appearing in text on communication devices 130 and 140, there is a central communication server 120 where all patient requests appear in chronological order in addition to level of urgency, displaying in full detail the patient's request, patient's key information, time request was made, responding nurse and time of response. All past requests can be achieved and searchable by patient number, bed number, nurse number, etc. These records can be used as cost and performance metrics for patients, nurses, section of the hospital, or for the entire hospital. The central communication server 120 controls all beside monitors for a particular unit and would also serve as the primary language center. From this station, the language of the patient communication device 110 can be chosen, changed, or altered. In addition, it can provide direct translation services. In the event the patient reads only Japanese and the nurse reads only English, the communication server 120 allows automatic translation between the patient communication device 110 and the nurse's desk or communication device 140, and also vice versa, allowing effective two way communication without the need of a translator. The communication server 120 also allows for voice communication between communication devices to be translated from one language to another when conversing between two languages.

The present method and system allows data for each patient to be entered prior to the patient's use of the patient communication device 110. The data may be entered using a keyboard, which connects to the system by wireless communication and/or by a wire connection. The present system may allow this data to be entered into the central communication system using an interactive touch screen and/or keyboard. Hospital staff are able to select the type of care administered to the patient (i.e., Triage/ER/EMS, ICU/ Recovery Room, General Med/Surg, Long-term Care/Hospice), the language spoken by the patient, the language spoken by the healthcare provider, the patient's name and general demographics (age, gender, etc.). The present system then presents menus to the patient that may vary according to these selections. For example, "ICU" could bring up a list of urgent needs associated with being unable to breathe, needing suctioning, having pain. In addition, this menu would provide dialog which would enable the expression of specific needs that are necessary for treatment that one would be unable to express without using their voice— as these patients are most often intubated and unable to speak. The communication deficit with these patients most often involves their inability to speak, whereas stable patients on a hospital ward are separated from their healthcare provider and their deficit lies in the inability of the healthcare provider to differentiate their needs from urgent and non-urgent prior to arriving to their room. Likewise, the preprogrammed text for acute (non-ICU) care would represent the communication needs for that patient population. This variation is consistent for each level of care the program supports. Again, the present method and system supports at least one level of care, possibly including more, four of which may be delineated as: Triage/ER/EMS, ICU/ Recovery Room, General Med/Surg, and Long-term Care/ Hospice.

The present method and system, according to one embodiment allows for verification of communications. All communications are automatically verified by the receiving device. Unverified messages are automatically resent after a programmable timeout period. Backup measures including sending a message to the system administrator and/or a secondary recipient are implemented after a programmable number of failed re-tries.

Another embodiment of the present invention comprises an advanced patient nurse call device. The present nurse call system utilizes 1) a bedside digital user interface (FIG. 4), lightweight handheld solutions for the providers (FIGS. 5A-5I), a nursing "whiteboard" (FIG. 6), and a software platform that uses an algorithm to enable patients, providers, and other ancillary staff the opportunity to communicate specific requests, remotely, instantly, and with pre-assigned priority rankings. The patient interface may have multiple screens (FIG. 7 and FIGS. 8A-D). The platform may also include functionalities that allow for precise monitoring of nurse call requests, patient admissions, transfers, and discharges, managing personnel/shift changes, and sign-offs from any PC with software or web access.

The present novel nurse call system offers a patient-centric interface (FIG. 4) that includes two hardware call buttons providing the option for urgent and non-urgent requests, and a touch screen (401) providing the option for making up to 30 specific requests. Call requests are routed based on provider availability, which for the present system, includes both real-time input from nursing staff as well as an automated algorithm that monitors the number and types of call requests assigned to each provider. Finally, the present system uses a combination of software and new hardware providing: 1) addition of bilingual communication; 2) two levels of call urgency; 3) a touch screen device for specifying requests allowing intelligent routing, and finally; 4) algorithmic routing of calls with unique capability for assessing provider availability remotely.

Figure 7:
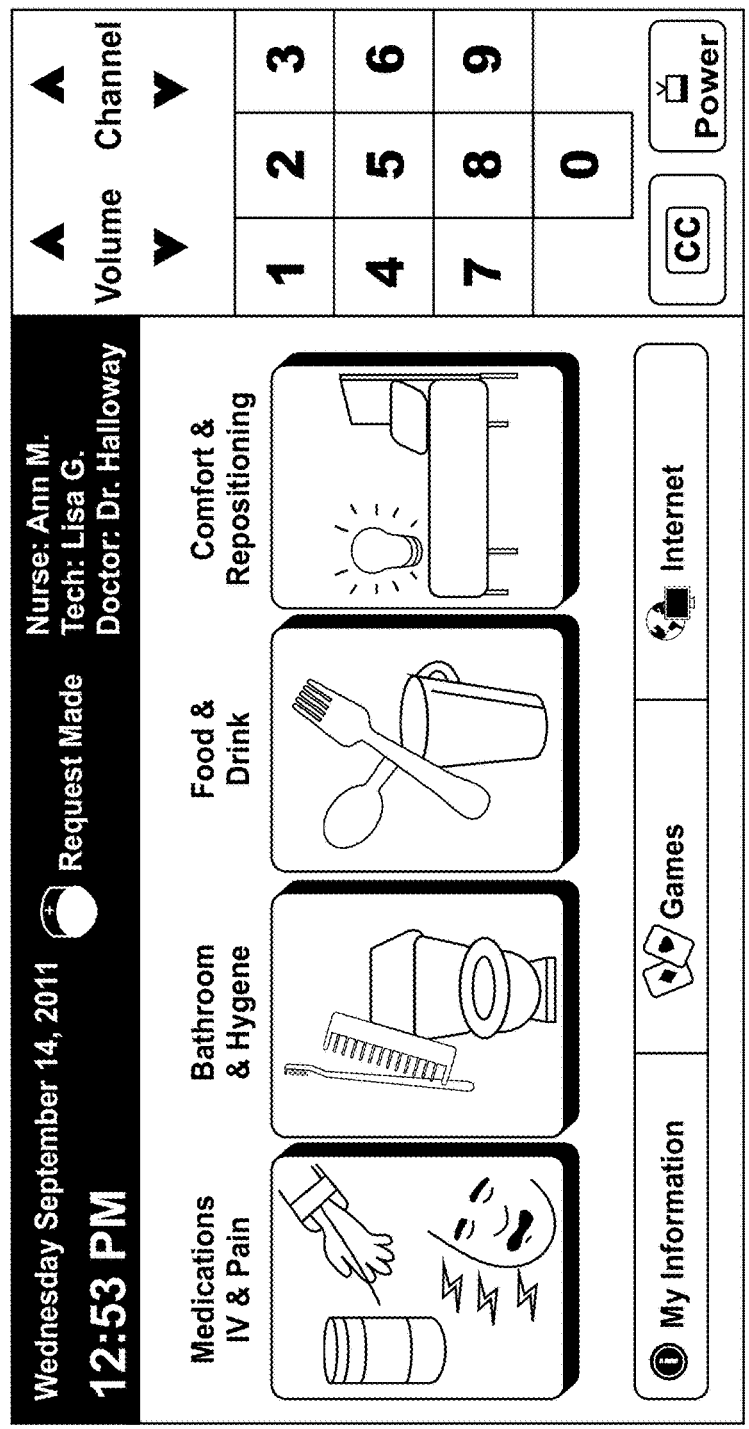
FIG. 7 is an exemplary main screen interface displaying categorical icons within an exemplary advanced pillow speaker, according to one embodiment.
Figure 8A:
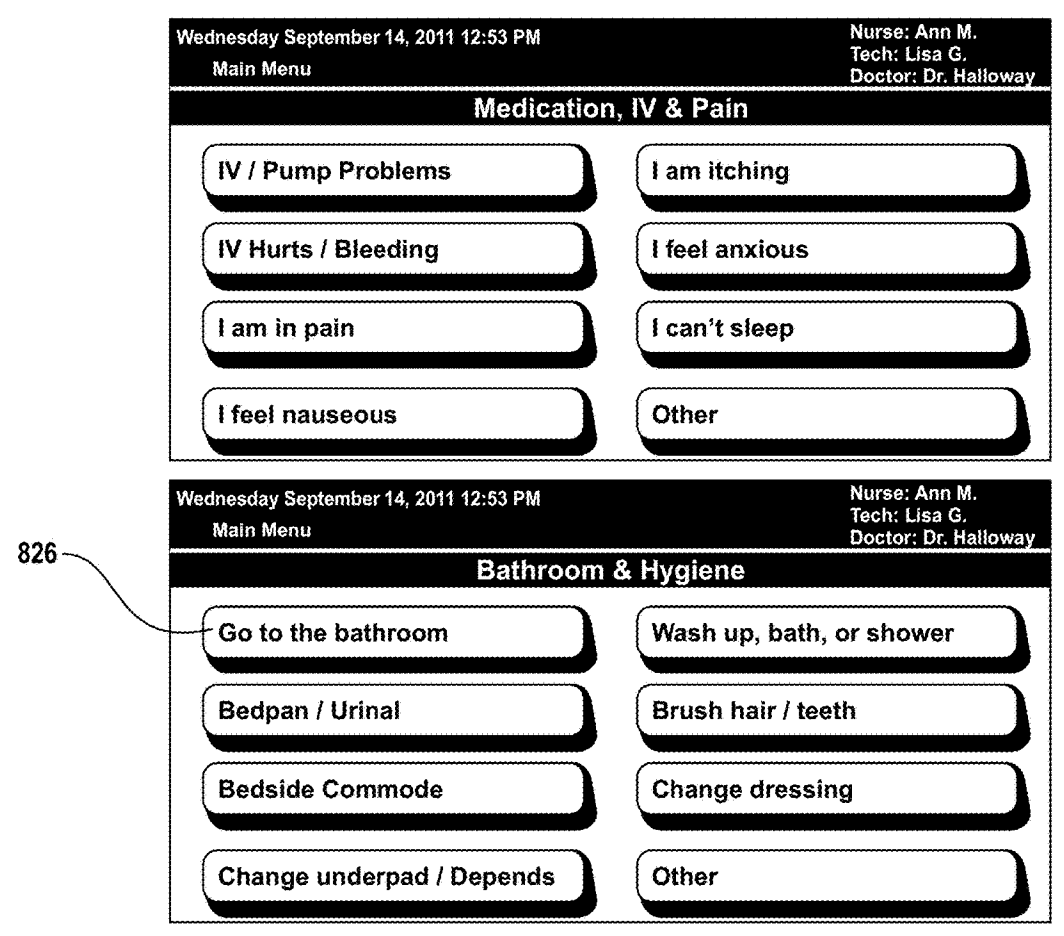
Figure 8B:
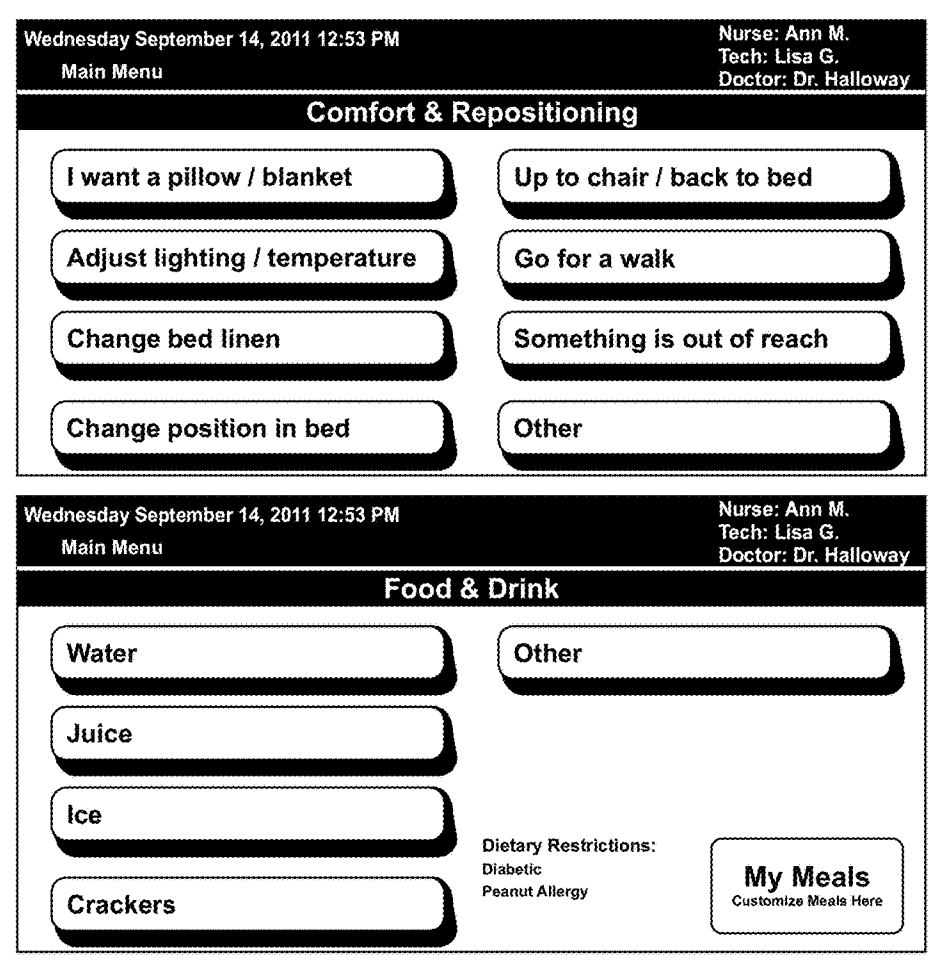
Figure 8D:
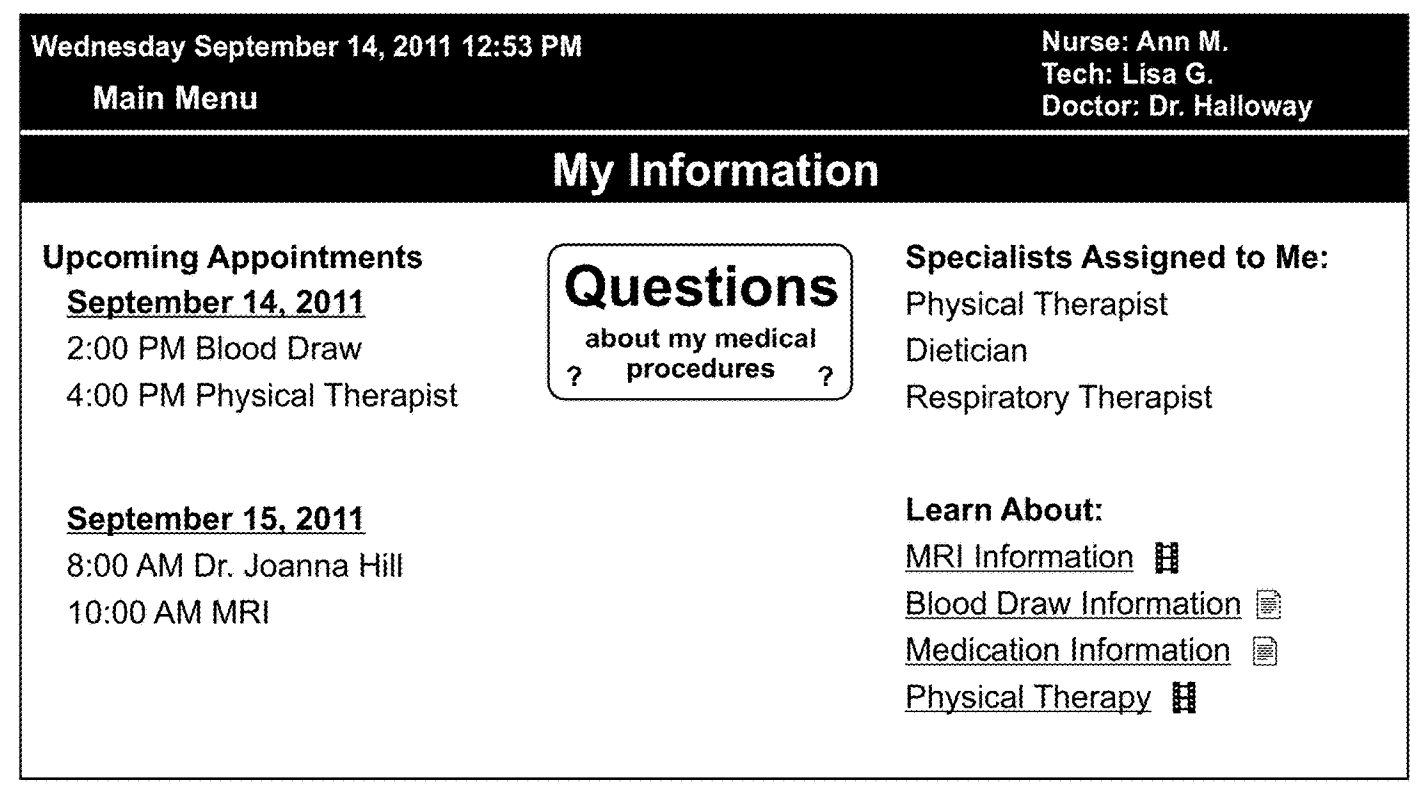

The patient touch screen displays four categorical requests: 1) IV, Medications & Pain (404); 2) Bathroom & Hygiene (405); 3) Food & Drink (406), 4) Comfort & Repositioning (407), organized according to skill level required to address the request within each category. This enables patients to select a category, which then delivers that specific message to their nursing staff, which is then communicated with a pre-assigned priority ranking and delivered to the most appropriate nursing personnel. A basic version only displays the categorical icons (FIG. 7). An advanced version displays a secondary screen after selecting each category (FIGS. 8A-D), providing more specific requests that correspond to category, with a total of thirty specific requests within all four categories. The present system also alerts the patient when a call request has been made and allows the patient to cancel their call if the request was made accidentally. This confirmation and cancellation process is not available on existing patient pillow speakers.

Figure 4:
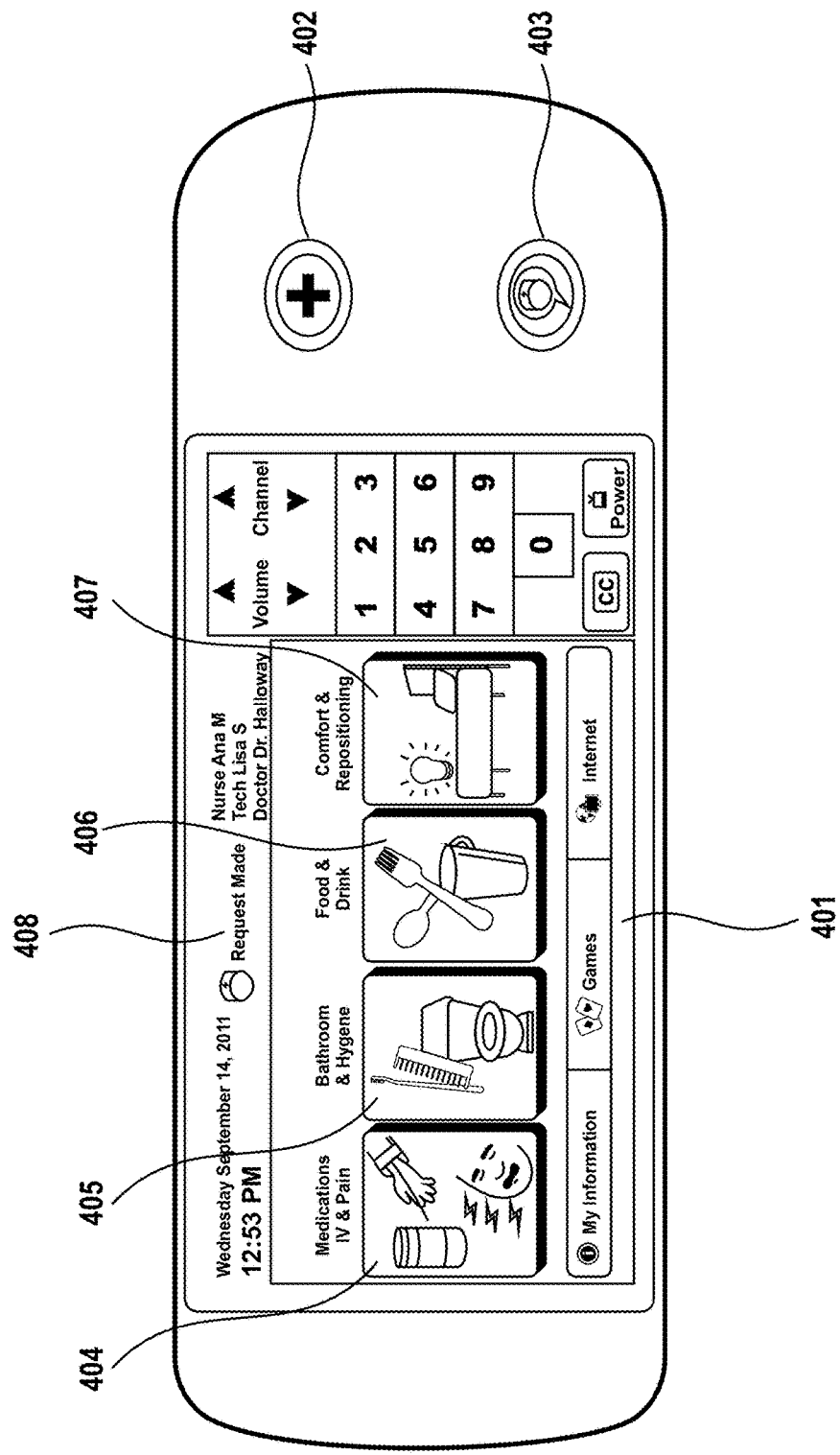
FIG. 4 is a front perspective view of an exemplary advanced pillow speaker, according to one embodiment.
Figure 5A:
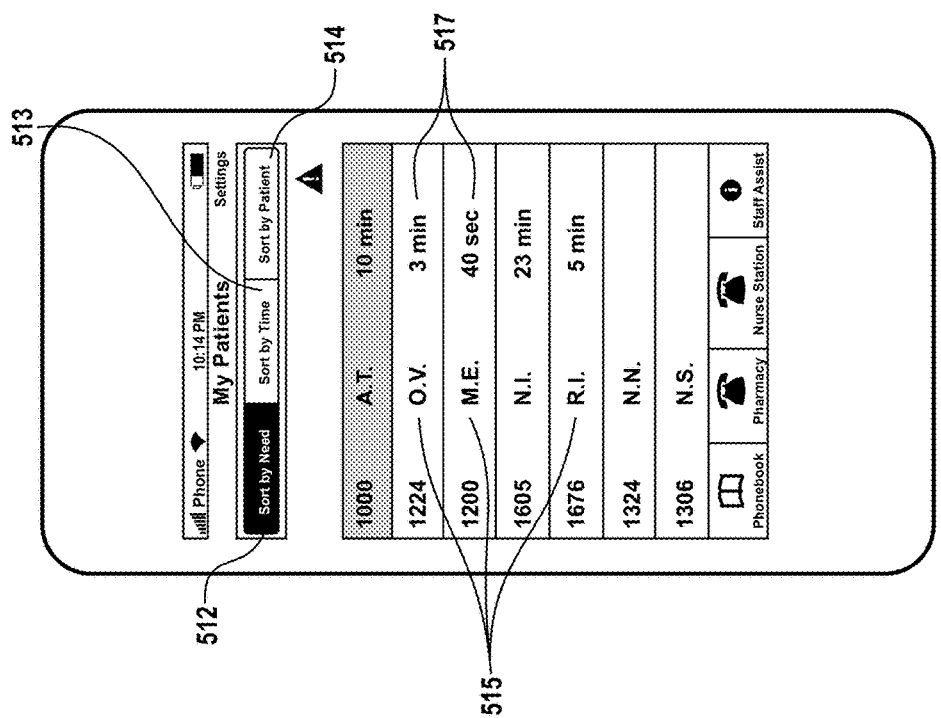
Figure 5B:
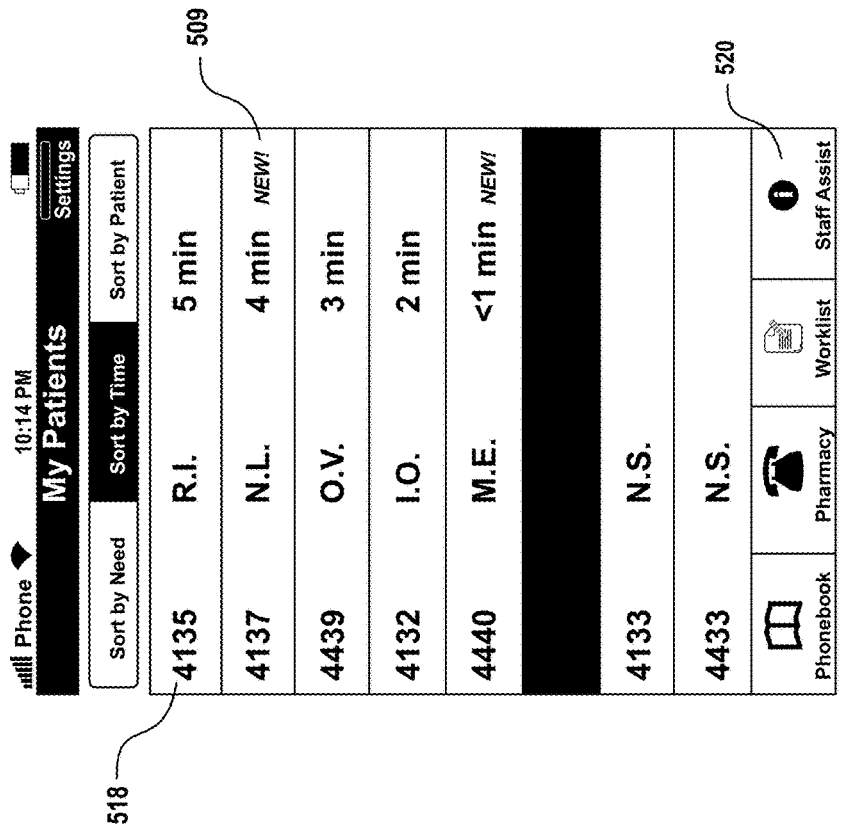
Figure 5C:
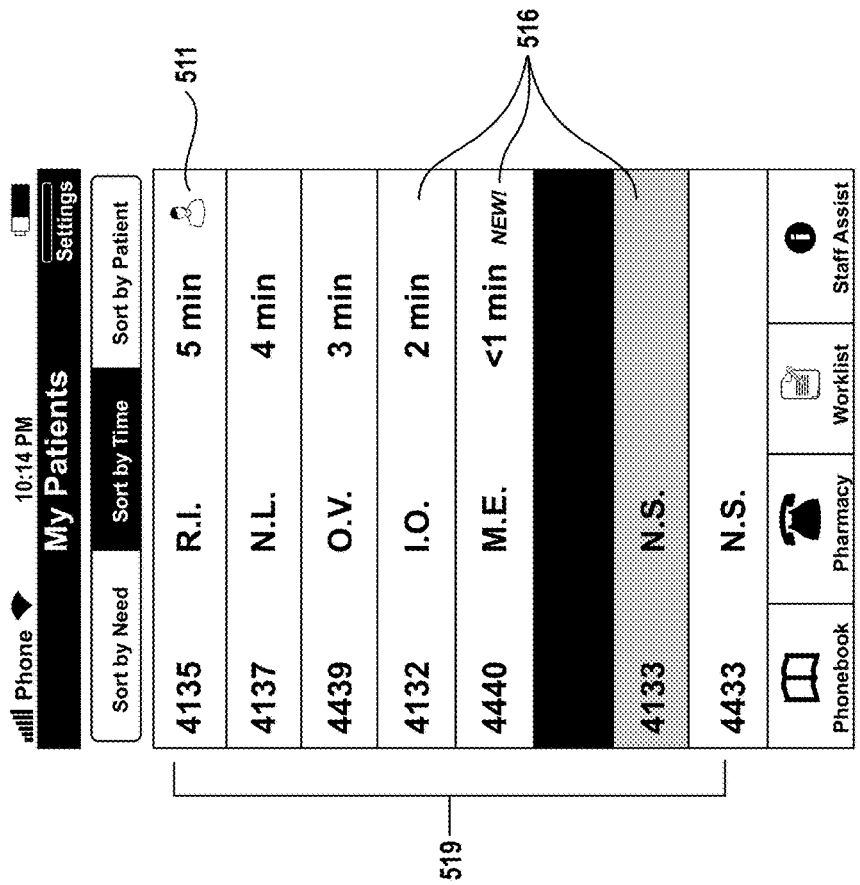
Figure 5D:
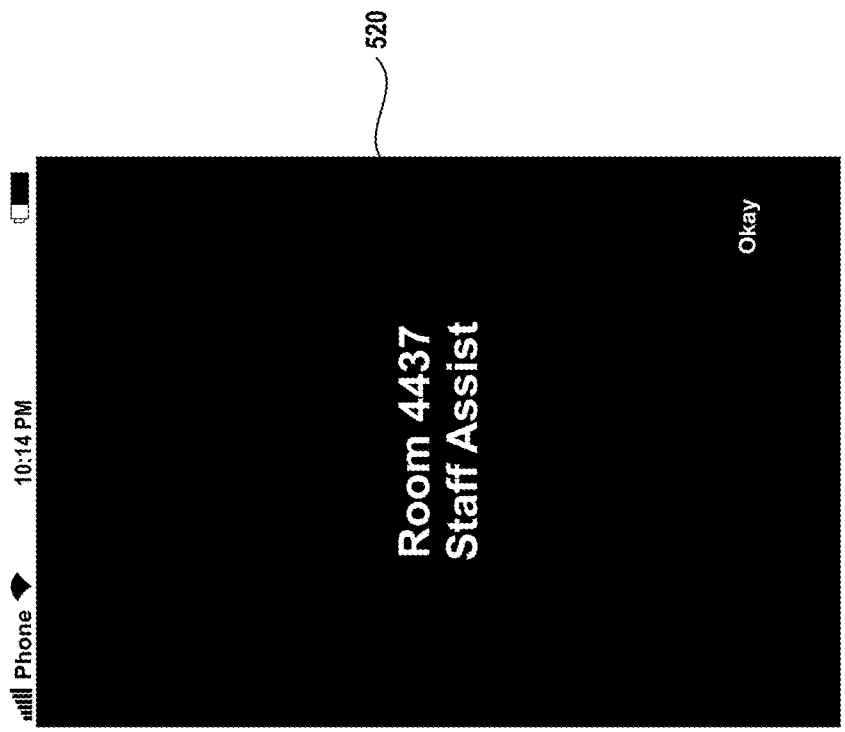
Figure 5E:
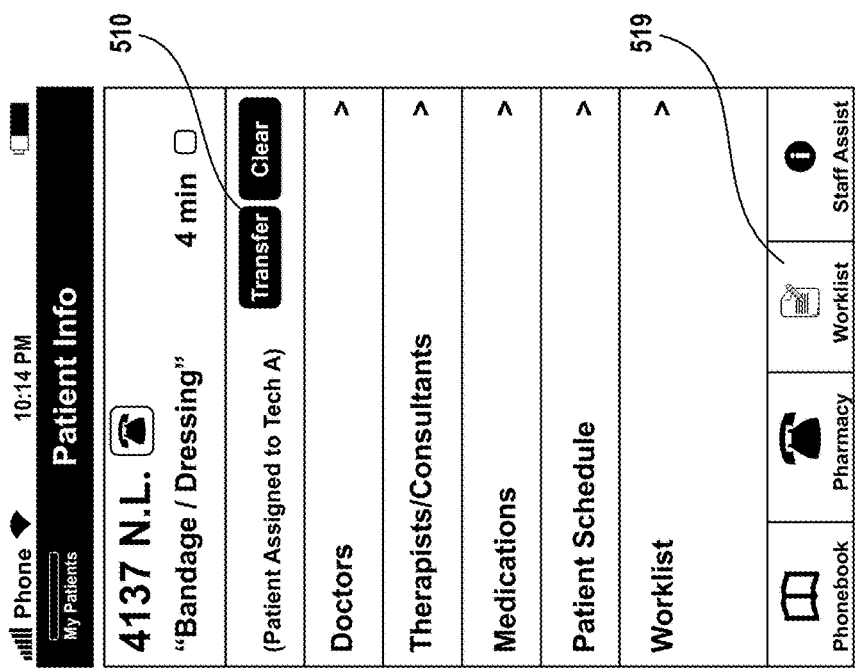
Figure 5F:
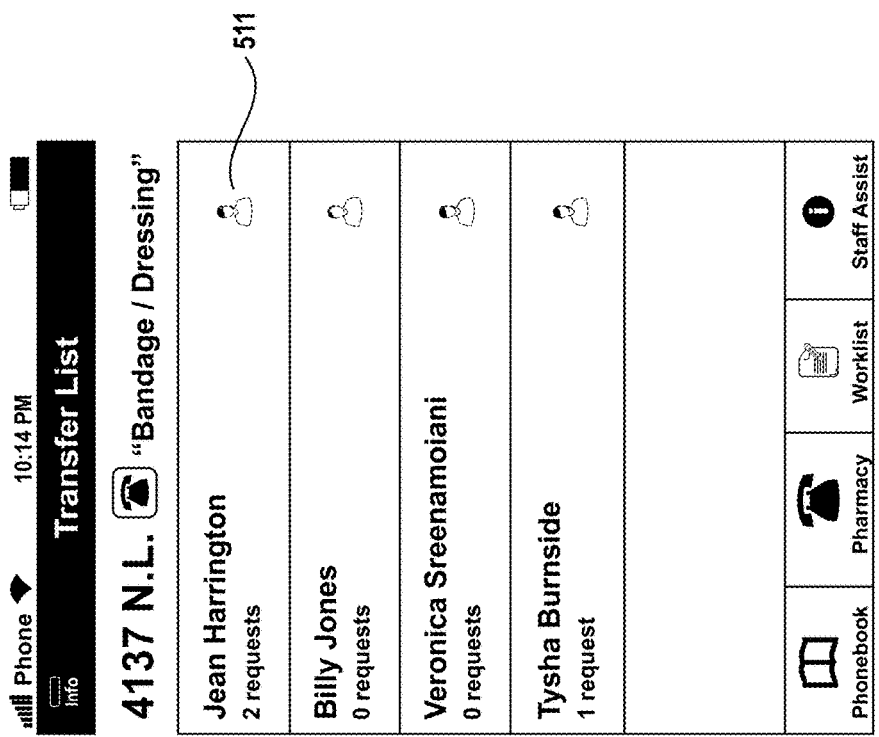
Figure 5I:
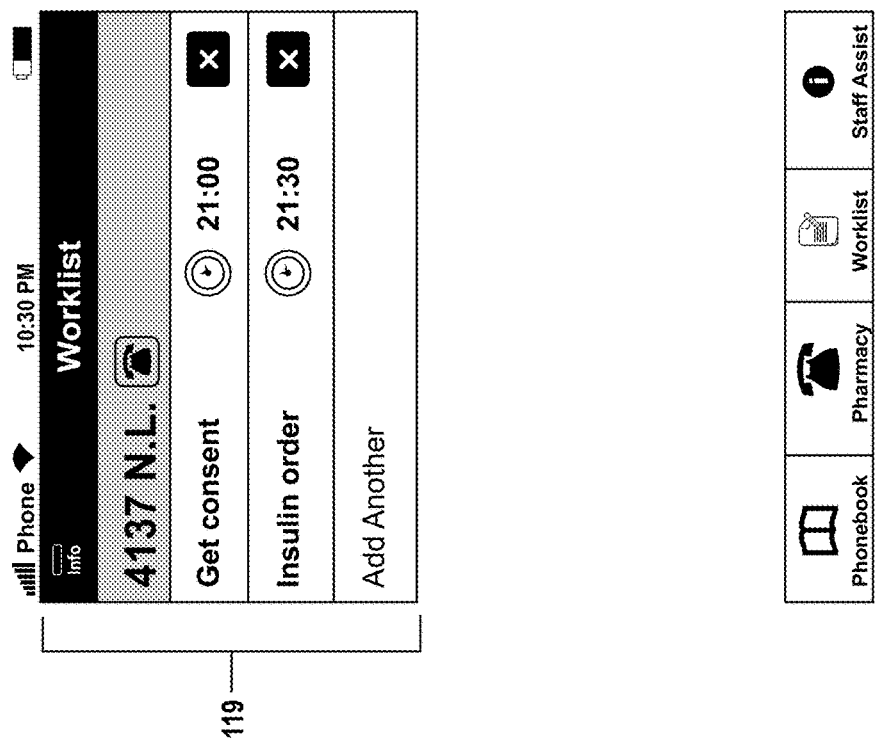

Referring now to the present system in more detail, in FIG. 4 there are shown two buttons (402 and 403). The lower button (403) provides the patient the opportunity to make a general or non-urgent call request while the top button (402) provides the patient the opportunity to make an urgent request. The functionality further provides the patient the opportunity to press the top button (402) after pressing the lower button (403) such that the patient who initially pressed the lower button (403) has now waited for some period of time and has recognized they no longer can wait and needs help right away. By doing so, the patient has now self-escalated their call request from non-urgent to urgent. These two buttons (402 and 403) may be positioned and distinguishable from one another in ways other than as displayed in FIG. 4, including the option for touch screen selectivity rather than depressing a physical hardware button.

In more detail, still referring to the embodiment of FIG. 4 there are shown two buttons (402 and 403). A pendant that is worn around the neck of the patient or around the patient's wrist having these two buttons, or providing at least one of these buttons, can be used when a patient is ambulating the halls, ambulating to the bathroom or sitting up in a chair where the bedside device in FIG. 4 would otherwise not be in reach. In this manner, the patient can initiate a call request remotely from this device.

In more detail, still referring to the embodiment of FIG. 4, a message "Request Made" (408) provides confirmation to the patient that they have successful initiated a call request.

In further detail, still referring to the embodiment of FIG. 4, the patient can, after initiating a call request, select the item a second time to cancel their request. After doing so, the patient is provided confirmation that their request has been cancelled by a message "Request Cancelled," which may appear in the same location as "Request Made" (408).

In further detail, still referring to the embodiment of FIG. 4, once a call request has been initiated, the provider's device messages to the provider that the request remains unacknowledged by the word "New" (509) in FIG. 5. Once the provider selects the call request from their handheld device, the call request no longer shows "New," indicating that the request has been acknowledged by the provider, and simultaneously sends a message to the patient device informing the patient that "Help is on the way," which may appear in the same location as "Request Made" (408).

Referring now to the embodiments shown in FIGS. 5A-5I, a message generated by a patient which is routed to an initial provider based on both the context of the message and the provider's skill level (Registered Nurse, Nurse Assistant) can be manually reassigned by the recipient to another provider from their receiving device or from another device that displays the message using the "Transfer" icon shown in 510. Once this call request has been transferred, a transferred icon appears on the list of call requests (511).

In more detail, still referring to the system of FIGS. 5A-I, providers are able to view their patients in order based on need (512), lapsed time (513), and by patient or room number (514).

In more detail, still referring to the embodiment of FIGS. 5A-I, a provider device displays a list of patients that can be color coded based on the call light request (515 and 516) and provider currently accountable to that request (515 and 516), and time since request was initiated (517) and the status of the request (initiated, acknowledged, in-progress, transferred to another provider, fulfilled).

In another embodiment, a provider device can comprise a touch screen display of patients which can be organized by urgency of request (512), by time elapsed since initiated (513), by room number (518), and by assigned provider type (516).

In another embodiment, a provider device can comprise a touch screen displaying the status of the call light request and the ability for the provider to choose to "respond," which can then both allow for direct voice communication with the patient and/or the patient's room and allow for communication by sending a text message which would appear on the patient's screen.

In another embodiment, a provider device can include the ability for the provider to change or update the status of the call light request (408) in FIG. 4.

In another embodiment, a provider device can comprise a touch screen whereby the recipient is able to redirect or transfer the request to another provider if the recipient of the request is unable to respond (510).

In another embodiment, for any call light request which has not been fulfilled, a provider device can automatically enter the request into and retain the request within a checklist which the provider can access and modify. The checklist can be sorted by patient or by time due, and can generate prompts/reminders (alarms) based on time due or manually scheduled times (519).

In another embodiment, a provider device can enable a provider to call for a Staff Assist, signaling the appropriate staff with both visual and audio queues on their devices as to the provider's location who initiated the Staff Assist (520).

Figure 6:
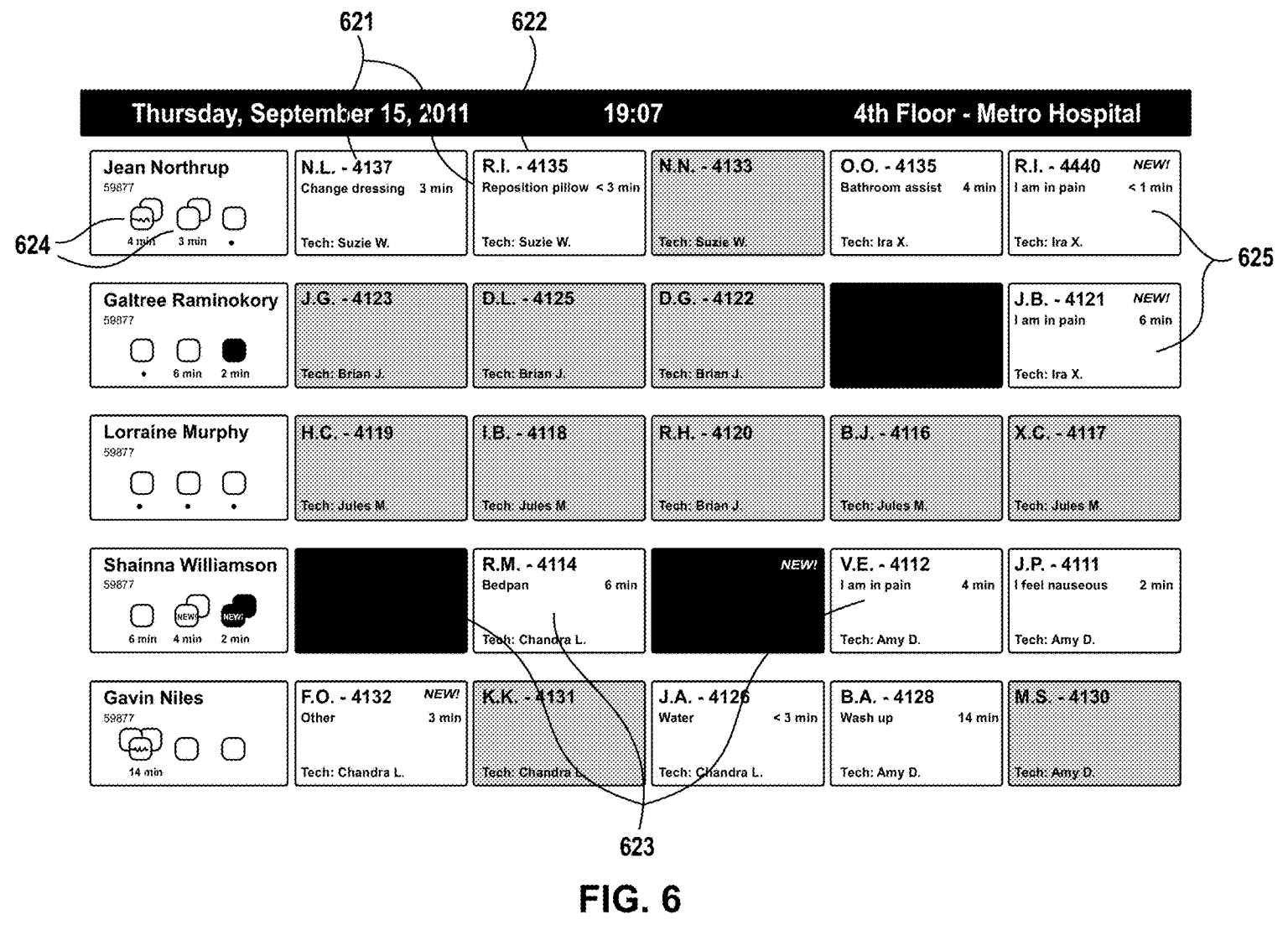

Referring now to the embodiment shown in FIG. 6, a display screen illustrates the context of each call light request (621) by location (622), the type of request (623), level of urgency of the request (623), status of request (e.g., initiated, acknowledged, in-progress, transferred to another provider, fulfilled) (625) and type of provider (624) that should first respond to the request for each patient, capable of organizing this information by provider and/or by patient room number and displaying this information accordingly, capable of providing call light reassignment from one provider to another.

In more detail, still referring to the embodiment of FIG. 6, a display screen illustrates the presence of a patient in their room, in their bathroom using RFID, and the presence of a provider, if the provider has entered the patient room, using RFID.

In another embodiment, a provider device can modify the status of a call light request if the provider associated with the provider device is the active recipient for that patient's active call light request. In yet another embodiment, the provider device can update the status of the type of provider making rounds, if the provider either assigned or qualified to perform patient rounds has entered the patient's room.

Referring now to the embodiments shown in FIGS. 7 and 8A-D, for patients who are determined to be at high risk of falling if they attempt to get out of bed on their own, the device shown in FIG. 4 would deliver a message to the patient if the patient initiated a categorical request such as "Bathroom & Hygiene" (405) or if the patient initiated a specific request such as "Go to the Bathroom" (826). The message delivered could be a textual message displayed on the screen shown in FIG. 7 or FIGS. 8A-D or a spoken message, such as "Please, do not get out of bed by yourself", or "You are at great risk of falling", or "Someone is on the way to help you" and might caution the patient from attempting to get up by themselves and prevent them from falling.

In more detail, still referring to the embodiments of FIG. 7 and FIGS. 8A-D, when a patient selects a message such as illustrated by 405 or 826, a message is generated by a patient device which is routed to an initial provider based on both the context of the message and the provider's skill level (Registered Nurse, Nurse Assistant). If the initial recipient has several other call requests which have not been fulfilled, the message can be automatically re-routed to another provider of like skill level based upon a programmable threshold having been reached, that threshold being a programmable number of unacknowledged requests, outstanding requests or unfulfilled requests of the initial provider/recipient.

In further detail, still referring to the embodiments of FIG. 7 and FIGS. 8A-D, when a patient selects a message such as illustrated by 405 or 826, a message generated by a patient device which is routed to an initial provider based on both the context of the message and the provider's skill level (Registered Nurse, Nurse Assistant, Physician) can be automatically re-routed to another provider of different skill level based upon a programmable threshold having been reached, that threshold being a programmable number of unacknowledged requests, outstanding requests or unfulfilled requests of either the initial provider/recipient or other providers/recipients of like skill level. In such a manner, the call request can be automatically routed and re-routed until it finds a recipient that would best be able to respond to the patient's request. The difference between what is stated here and previously stated above is that the destination of automatic routing and re-routing, as described above, may be a recipient that is not the best match with respect to the best skill level to fulfill the request, but it provides the opportunity for a provider to at least attend to the patient if a provider that does match the skill necessary to fulfill the request is not available.

In further detail, still referring to the embodiments of FIG. 4, FIG. 7 and FIGS. 8A-D, a patient pillow speaker device that provides the patient with more than one contextually specific nurse call request, whereby more than one request (404-407, or 404 and 826) can be active simultaneously, whereby the recipient(s) of such request may be notified of the context of each request with a plurality of requests; whereby the initial recipient(s) of each request can be routed or automatically re-routed based on the context of each message, the skill level required to fulfill each request, the skill level of the recipient and the number of unacknowledged requests, outstanding requests or unfulfilled requests of the initial provider/recipient.

Referring now to the embodiments shown in FIG. 4 through FIG. 8D, all textual content can be provided in a multilingual format allowing the spoken language of the patient to be selected within the setup process, which would then display all textual content in the patient's preferred language. This continues to send the same message to the providers allowing the providers to understand the patient's needs initiated in the patient's preferred language and read by the provider in the provider's preferred language.

The advantages of the present invention include, without limitation, a change in clinical practice by providing nurses a way to streamline patient care, work more efficiently, and provide a safer, more satisfying patient experience. Although there have been other attempts to develop structural work role redesigns by providing patient communication metrics, a workflow redesign could optimally remove non-value added time from licensed nursing personnel. When nurses know the patient's specific need when the call button is initiated, the response can be prioritized and/or redirected to appropriate staff (skilled vs. non-skilled), bypassing the need for triaging call requests, thereby improving patient safety and efficiency of care. In this manner, the present invention may impact nursing shortage by providing administration optimal allocation of nursing resources through unique workflow management features that allow administration to examine the types of call requests and associated required nursing personnel. Since the difference in full-time equivalent staffing expenses paid to Registered Nurses and nurse assistants is roughly $80,000-$100,000, depending on location within the United States, this reallocation of staffing resources can produce significant cost-savings. It is therefore possible that a 500-bed hospital can save $1 M-$1.5 M annually through implementation of the present system. Further, by providing nursing staff a digital record of the patient's request on their handheld device, it provides a safety net relieving nursing staff from relying on their memory or handwritten lists of tasks, thereby reducing human error. Anticipated benefits from the present system for both patients and healthcare organizations are a reduction in adverse patient events, such as falls, and improvements in provider efficiencies.

In another embodiment, the present system is an enhanced pillow speaker that identifies the specific context of each patient request along with an algorithm to deliver a specific message to the hospital nursing staff with a pre-assigned priority ranking based on the urgency of the request and skill level required to fulfill the patient request. There are two patient- and nurse-centric aspects of the present system solution that truly differentiate the present system from other nurse call technologies: 1) the specificity of messages being sent from the patient's pillow speaker (FIGS. 5A-5I), and 2) the algorithm used to manage these messages. With the present system, the patient's specific need is delivered to the most appropriate nursing personnel for immediate response, without requiring a staff member to triage the request. By providing patient- and nurse-centric categorizations via textual or pictorial icons at the patient bedside, patient call requests can, for the first time, be routed to the most appropriate and available provider without the requirement of a staff member to first triage the request.

In the description above, for purposes of explanation only, specific nomenclature is set forth to provide a thorough understanding of the present disclosure. However, it will be apparent to one skilled in the art that these specific details are not required to practice the teachings of the present disclosure.

Some portions of the detailed descriptions herein are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the below discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms presented herein are not inherently related to any particular computer or other apparatus. Various general purpose systems, computer servers, or personal computers may be used with programs in accordance with the teachings herein, or it may prove convenient to construct a more specialized apparatus to perform the required method steps. The required structure for a variety of these systems will appear from the description below. It will be appreciated that a variety of programming languages may be used to implement the teachings of the disclosure as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

A method and system for advanced patient communication have been described. An advanced patient nurse call device has also been disclosed. It is understood that the embodiments described herein are for the purpose of elucidation and should not be considered limiting the subject matter of the present patent. Various modifications, uses, substitutions, combinations, improvements, methods of productions without departing from the scope or spirit of the present invention would be evident to a person skilled in the art.

We claim:

1. A patient communication device, comprising:
   a selection input mechanism with a display for presenting a plurality of messages and enabling a patient to select at least one of the presented messages via touching the display or at least one display navigation control button to generate a message reflecting a patient request and an urgency level associated with the patient request;
a transmitter for transmitting the message to a central processing server; and
a status indicator representing a transmission status associated with the message,
wherein the message is initially routed to a first provider based upon a context of the patient request, the urgency level, a skill level or role of the first provider or a combination thereof, and
wherein the message then is routed to a second provider with a skill level that is comparable to the skill level of the first provider.

2. The patient communication device of claim 1, wherein the message is automatically routed to the first provider based upon the context of the patient request, the urgency level, the skill level or role of the first provider or a combination thereof.

3. The patient communication device of claim 1, wherein the message is routed to the second provider based upon a predetermined threshold being reached.

4. The patient communication device of claim 3, wherein the message is routed to the second provider with a skill level that is equal to the skill level of the first provider.

5. The patient communication device of claim 3, wherein the message is routed to the second provider with a skill level that is different from the skill level of the first provider.

6. The patient communication device of claim 3, wherein the predetermined threshold includes a first predetermined number of requests that have not been acknowledged by the first provider, a second predetermined number of outstanding requests for the first provider, a third predetermined number of requests that have not been fulfilled by the first provider or a predetermined time lapse from when the generated message occurred.

7. The patient communication device of claim 6, wherein the first predetermined number, the second predetermined number or the third predetermined number is a programmable number.

8. The patient communication device of claim 1, wherein the first provider is selected from a group consisting of a registered nurse, a nurse assistant, a physician, or a combination thereof.

9. The patient communication device of claim 1, wherein said selection input mechanism is capable of adjusting the urgency level of the patient request.

10. The patient communication device of claim 1, wherein said selection input mechanism is capable of adjusting the urgency level of the patient request after the message has been transmitted to the central processing server.

11. The patient communication device of claim 1, wherein said status indicator is updatable to represent a current process status of the message.

12. The patient communication device of claim 1, wherein said selection input mechanism is capable of preventing the message from being cancelled by the patient.

13. A patient communication device, comprising:
a selection input mechanism with a display for presenting a plurality of messages and enabling a patient to select at least one of the presented messages via touching the display or at least one display navigation control button to generate a message reflecting a patient request and an urgency level associated with the patient request; and
a status indicator representing a transmission status associated with the message and being updatable to represent a current process status of the message,
wherein the message is initially routed to a first provider based upon a context of the patient request, the urgency level, a skill level of the first provider or a combination thereof, and
wherein the message then is routed to a second provider with a skill level that is comparable to the skill level of the first provider.

14. The patient communication device of claim 13, wherein said selection input mechanism includes a button, keyboard, a touch screen or a combination thereof.

15. The patient communication device of claim 13, further comprising a transmitter for transmitting the message to a central processing server.

16. The patient communication device of claim 13, wherein said selection input mechanism enables an authorized caregiver to enter an order for a procedure, a consult, or a medication or indication that the patient request is complete, and wherein said status indicator represents the order or indication of the caregiver.

17. A patient communication device, comprising:
a selection input mechanism with a display for presenting a plurality of messages, enabling a patient to select at least one of the presented messages via touching the display or at least one display navigation control button to generate a message that is unable to be cancelled by the patient, the message reflecting a patient request and an urgency level associated with the patient request; and
a transmitter for transmitting the message to a central processing server,
wherein the message is initially routed to a first provider based upon a context of the patient request, the urgency level, a skill level of the first provider or a combination thereof, and
wherein the message then is routed to a second provider with a skill level that is comparable to the skill level of the first provider.

18. The patient communication device of claim 17, wherein said selection input mechanism includes a button, keyboard or a touch screen or a combination thereof.

19. The patient communication device of claim 17, further comprising a status indicator on the display representing a transmission status associated with the message.

20. The patient communication device of claim 17, wherein said selection input mechanism enables an authorized caregiver to enter an order for a procedure, a consult, or a medication or indication that the patient request is complete, and wherein said status indicator represents the order or indication of the caregiver.

21. A patient communication device, comprising:
a selection input mechanism with a display for presenting a plurality of messages and enabling a patient to select at least one of the presented messages via touching the display or at least one display navigation control button to generate a message reflecting a patient request and an urgency level associated with the patient request,
wherein the message is initially routed to a first provider based upon a context of the patient request, the urgency level, a skill level of the first provider or a combination thereof, and
wherein the message then is routed to a second provider with a skill level that is comparable to the skill level of the first provider.

22. A patient communication device, comprising:
a selection input mechanism with a display for presenting a plurality of messages and enabling a patient to select at least one of the presented messages via touching the display or at least one display navigation control button to generate a message reflecting a patient request and an urgency level associated with the patient request, wherein the message is initially routed to a first provider based upon a context of the patient request, the urgency level, a skill level of the first provider or a combination thereof, and wherein the message then is routed to a second provider with a skill level that is different from the skill level of the first provider.

* * * * *